(12) United States Patent
Wise et al.

(10) Patent No.: US 10,608,400 B2
(45) Date of Patent: Mar. 31, 2020

(54) FIBER SOURCE OF SYNCHRONIZED PICOSECOND PULSES FOR COHERENT RAMAN MICROSCOPY AND OTHER APPLICATIONS

(71) Applicant: Cornell University, Ithaca, NY (US)

(72) Inventors: Frank Wise, Ithaca, NY (US); Simon Lefrancois, Quebec (CA)

(73) Assignee: Cornell University, Ithaca, NY (US)

(*) Notice: Subject to any disclaimer, the term of this patent is extended or adjusted under 35 U.S.C. 154(b) by 0 days.

(21) Appl. No.: 14/350,062

(22) PCT Filed: Oct. 4, 2012

(86) PCT No.: PCT/US2012/058817
§ 371 (c)(1),
(2) Date: Apr. 4, 2014

(87) PCT Pub. No.: WO2013/052711
PCT Pub. Date: Apr. 11, 2013

(65) Prior Publication Data
US 2014/0247448 A1 Sep. 4, 2014

Related U.S. Application Data

(60) Provisional application No. 61/652,805, filed on May 29, 2012, provisional application No. 61/543,295, filed on Oct. 4, 2011.

(51) Int. Cl.
*H01S 3/108* (2006.01)
*G02F 1/35* (2006.01)
(Continued)

(52) U.S. Cl.
CPC ............ *H01S 3/1083* (2013.01); *G01J 3/10* (2013.01); *G01J 3/44* (2013.01); *G01N 21/65* (2013.01);
(Continued)

(58) Field of Classification Search
CPC ................ H01S 3/1083; G02F 1/3536; G02F 2001/392; G02F 1/3538; G01N 2021/653
See application file for complete search history.

(56) References Cited

U.S. PATENT DOCUMENTS 5,606,453 A * 2/1997 Walling .................... G02F 1/39
359/256
5,717,510 A * 2/1998 Ishikawa ............... H04L 7/0037
398/147
(Continued)

FOREIGN PATENT DOCUMENTS

WO 2007127356 11/2007

OTHER PUBLICATIONS

Ahn, J. Y., Authorized Officer, Korean Intellectual Property Office, International Search Report and Written Opinion, International Application No. PCT/US2012/058817, dated Mar. 13, 2013, 7 pages.

(Continued)

*Primary Examiner* — Tod T Van Roy
*Assistant Examiner* — Sean P Hagan
(74) *Attorney, Agent, or Firm* — Perkins Coie LLP

(57) ABSTRACT

Devices and techniques that use nonlinear optical effects in optical fiber to generate optical pulses via nonlinear optical wave mixing for various applications such as coherent Raman microscopic measurements and optical parametric oscillators. In some implementations, a tunable optical delay path is provided to cause an adjustable delay for synchronizing two optical beams of optical pulses.

23 Claims, 14 Drawing Sheets

Seeded FWM setup. A PCF is used for the normal dispersion engineered fiber

(51) Int. Cl.
- G02F 1/39 (2006.01)
- G01J 3/10 (2006.01)
- G01J 3/44 (2006.01)
- H01S 3/23 (2006.01)
- H01S 3/00 (2006.01)
- G01N 21/65 (2006.01)

(52) U.S. Cl.
CPC ............ *G02F 1/3536* (2013.01); *G02F 1/395* (2013.01); *G01N 2021/653* (2013.01); *G02F 2001/392* (2013.01); *H01S 3/0092* (2013.01); *H01S 3/2391* (2013.01)

(56) References Cited

U.S. PATENT DOCUMENTS

| | | | |
|---|---|---|---|
| 6,330,104 B1 | 12/2001 | Kim et al. | |
| 6,710,914 B2* | 3/2004 | Arbore | G02F 1/39 359/330 |
| 8,385,699 B2* | 2/2013 | Liu | G02B 6/02214 359/341.1 |
| 2002/0001321 A1* | 1/2002 | Perry | B23K 26/12 372/22 |
| 2006/0192969 A1* | 8/2006 | Marks | G01J 3/4412 356/451 |
| 2006/0198397 A1 | 9/2006 | Korolev et al. | |
| 2006/0239604 A1* | 10/2006 | Marhic | G02F 1/395 385/13 |
| 2007/0035810 A1* | 2/2007 | Henderson | H01S 3/0675 359/330 |
| 2007/0206272 A1* | 9/2007 | Ono | G02F 1/395 359/330 |
| 2009/0141281 A1* | 6/2009 | Stothard | G01N 21/35 356/437 |
| 2010/0085992 A1 | 4/2010 | Rakuljic et al. | |
| 2010/0142034 A1* | 6/2010 | Wise | H01S 3/0057 359/349 |
| 2011/0013268 A1* | 1/2011 | Shaw | H01S 3/06741 359/341.1 |

OTHER PUBLICATIONS

Andresen, E.R. et al., "Fiber laser-based light source for coherent anti-Stokes Raman scattering microspectroscopy," Opt. Express 15, 2007, pp. 4848-4856.

Begin, S. et al., "Coherent anti-Stokes Raman scattering hyperspectral tissue imaging with a wavelength-swept system", Biomedical Optics Express, 2011, vol. 2, No. 5, pp. 1296-1306.

Cocuzzi et al., "Narrow-Bandwidth, Subnanosecond, Infrared Pulse Generation in PPLN Pumped by a Fiber Amplifier-Microchip Oscillator". IEEE Journal of Selected Topics in Quantum Electronics 15, pp. 372-376, (2009).

Duncan, M.D. et al., "Scanning Coherent Anti-Strokes Raman microscope", Opt. Lett. 1982, vol. 7, pp. 350-352.

Freudiger, C.W. et al., "Label-Free Biomedical Imaging with High Sensitivity by Stimulated Raman Scattering Microscopy," Science 322, 2008, pp. 1857-1861.

Ganikhanov, F. et al., "Broadly tunable dual-wavelength light source for coherent anti-Stokes Raman scattering microscopy," Opt. Lett. 31, 2006, vol. 31, No. 9, pp. 1292-1294.

Gu, C. et al., "Cross-phase-modulation-induced spectral effects in high-efficiency picosecond fiber optical parametric oscillators", Optics Letters, 2011, vol. 36, No. 8, pp. 1488-1490.

Kee, T.W. et al., "Simple approach to one-laser, broadband coherent anti-Stokes Raman scattering microscopy," Opt. Lett. 29, 2004, pp. 2101-2103.

Kieu, K. et al., "High-power picosecond fiber source for coherent Raman microscopy", Optics Letters, 2009, vol. 34, No. 13, pp. 2051-2053.

Kieu, K. et al., "Synchronized picosecond pulses at two different wavelengths from a compact fiber laser source for Raman microscopy", Proc. of SPIE vol. 7903, 7390310-1.

Krauss, G. et al., "Compact coherent anti-Stokes Raman scattering microscope based on a picosecond two-color Er: fiber laser system", Optics Letters, 2009, vol. 34, No. 18, pp. 2847-2849.

Lavoute et al., "High Power Red and Near-OR generation Using Four Wave Mixing in All Integrated Fibre Laser Sytems", Optics Express, 18, 2010, pp. 16193.

Lefrancois, S. et al., "Fiber four-wave mixing source for coherent anti-Stokes Raman scattering microscopy", Optics Letters, 2012, vol. 37, No. 10, pp. 1652-1654.

Pestov, D. et al., Optimizing the Laser-Pulse configuration for Coherent Raman Spectroscopy, Science 316, 2007, pp. 265-268.

Ploetz, E. et al., "Femtosecond stimulated Raman microscopy," Appl. Phys. B 87, 2007, pp. 389-393.

Potma, E.O. et al., "High-sensitivity coherent anti-Stokes Raman scattering microscopy with two tightly synchronized picosecond lasers," Opt. Lett. 27, 2002, pp. 1168-1170.

Zhai, Y.H. et al., "Multimodal coherent anti-Stokes Raman spectroscopic imaging with a fiber optical parametric oscillator", Appl. Phys. Lett. 98, 2011, pp. 191106-1-191106-3.

Zhou, S. et al., "Divided-pulse amplification of ultrashot pulses", Optics Letters, 2007, vol. 2, No. 7, pp. 871-873.

Zumbusch, A. et al., "Three-dimensional vibrational imaging by coherent anti-Stokes Raman scattering", Phys. Rev. Lett. 1999, vol. 82, pp. 4142-4144.

* cited by examiner

Schematic of the CARS process

*Calculated FWM gain (left) and phase-matching (right) for PCF, with 5 kW of pump peak power*

Simulations of seeded FWM after 18 cm of PCF. Input pump pulse: 7 ps and 5 kW peak power. A seed power of 10 mW at 1465 nm is assumed.

Seeded FWM setup. A PCF is used for the normal dispersion engineered fiber

Results of proof-of-concept experiment. Power spectra of signal (left), residual pump (center) and idler plus seed (right) are shown.

Measured autocorrelation (left) and spectral broadening (right) of 774 nm signal

*RF spectra of the FWM signal seeded by an amplified semiconductor laser (left) and an Er fiber laser (right).*

FIBER SOURCE OF SYNCHRONIZED PICOSECOND PULSES FOR COHERENT RAMAN MICROSCOPY AND OTHER APPLICATIONS

PRIORITY CLAIMS AND RELATED PATENT APPLICATIONS

This patent document claims priorities and benefits of U.S. Provisional Application No. 61/543,295 entitled "FIBER SOURCE OF SYNCHRONIZED PICOSECOND PULSES FOR COHERENT RAMAN MICROSCOPY AND OTHER APPLICATIONS" filed Oct. 4, 2011, and U.S. Provisional Patent Application No. 61/652,805 entitled "FIBER-FEEDBACK OPTICAL PARAMETRIC OSCILLATORS BASED ON FIBER SOURCE OF SYNCHRONIZED PICOSECOND PULSES" filed May 29, 2012. The disclosures of the above patent applications are incorporated by reference as part of the disclosure of this document.

STATEMENT OF GOVERNMENT SUPPORT

This invention was made with government support under Grant No. EB002019 awarded by the National Institutes of Health (NIH) and under Grant No. BIS-0967949 awarded by the National Science Foundation (NSF). The government has certain rights in the invention.

TECHNICAL FIELD

This patent document relates to devices and techniques for using optical fiber to generate optical pulses via nonlinear optical wave mixing.

BACKGROUND

Optical fiber can be used in various applications and, like many other optical media, optical fiber exhibits nonlinear optical effects. Nonlinear optical effects in optical fiber can lead to undesired consequences, such as optical signal distortions in fiber optical networks. On the other hand, nonlinear optical effects in optical fiber can also be advantageously used to achieve certain beneficial technical results for various applications. For example, four wave mixing effects in optical fiber can be used for certain signal processing and for generation of frequency-shifted coherent signals, including constructing fiber-based optical parametric amplifiers and optical parametric amplifiers.

SUMMARY

This patent document discloses devices and techniques that use nonlinear optical effects in optical fiber to generate optical pulses via nonlinear optical wave mixing for various applications such as coherent Raman microscopic measurements and optical parametric oscillators.

In one aspect, an optical device is provided for producing optical pulses based on four wave mixing. This device includes a pump laser module to produce a pump laser beam having pump laser pulses at a pump laser wavelength; a segment of fiber having an input port and an output port, the input port coupled to receive the pump laser beam and configured to exhibit normal optical dispersion as a nonlinear optical four wave mixing medium to convert energy at the pump laser wavelength into a four wave mixing signal at a signal wavelength shorter than the pump laser wavelength and an idler signal at an idler wavelength longer than the laser pump wavelength; a seed laser coupled to the input port of the segment of fiber to inject seed laser light at the idler wavelength with a narrow spectral width into the segment of fiber to coexist with the pump laser pulses inside the segment of fiber as a seed for initiating the idler signal for the four wave mixing in the segment of fiber; a pump delay path coupled to receive a portion of the pump laser beam as a bypass pump laser beam that does not enter the segment of fiber; and an output port coupled to the output port of the segment of fiber to select the four wave mixing signal at the signal wavelength from light output by the segment of fiber as a signal output without including light at a wavelength different from the signal wavelength, and coupled to the pump delay path to receive the bypass pump laser beam, the output port configured to combine the bypass pump laser beam and the four wave mixing signal as a 2-color output.

In another aspect, an optical device for producing optical pulses is provided to include a source laser to produce laser pulses at a first laser wavelength; a segment of fiber coupled to receive the laser pulses and configured to exhibit normal optical dispersion as a nonlinear optical four-wave mixing medium, where seed laser light at a second laser wavelength different from the first laser wavelength in the segment of fiber coexists with the laser pulses inside the segment of fiber to cause generation of light at a third laser wavelength via nonlinear four-wave mixing inside the segment of fiber; and an optical feedback path that feeds a portion of generated light at the third laser wavelength back to the segment of fiber to mix with the light at the first wavelength, and the seed light at the second wavelength, wherein the optical feedback is configured to sustain an optical parametric oscillation. In implementations, the device may include a tunable optical delay path that receives a portion of the light of the laser pulses from the source laser and directs the portion of light to combine with the output of the segment of fiber to produce a synchronized output. The device may also include an optical bandpass filter placed in the optical feedback path to remove light at wavelengths other than the third wavelength from the optical feedback path.

In another aspect, a method for generating optical pulses is provided to include operating a source laser to produce laser pulses at a first laser frequency; coupling a segment of fiber which exhibits normal optical dispersion and is a nonlinear optical four-wave mixing medium to receive the laser pulses to mix with seed laser light at a second laser frequency different from the first laser frequency inside the segment of fiber to cause generation of light at a third laser frequency via nonlinear four-wave mixing inside the segment of fiber; and feeding a portion of generated light at the third laser wavelength back to the segment of fiber to mix with the light at the first wavelength, and the seed light at the second wavelength to sustain an optical parametric oscillation.

In another aspect, an optical fiber source for producing optical pulses is provided to include a fiber laser to produce laser pulses at a first laser wavelength; a fiber optical amplifier placed downstream from the fiber laser to receive the laser pulses and to amplify the laser pulses; a segment of fiber coupled to receive the amplified laser pulses from the fiber optical amplifier and configured to exhibit normal optical dispersion as a nonlinear optical four-wave mixing medium; and a seed laser coupled to the segment of fiber to inject seed laser light at a second laser wavelength different from the first laser wavelength into the segment of fiber to coexist with the amplified laser pulses inside the segment of fiber to cause generation of a first optical pulse at the first laser wavelength and a second optical pulse at a third laser wavelength generated via nonlinear four-wave mixing inside the segment of fiber.

In another aspect, a method for performing Raman imaging is provided to include operating a fiber laser to produce laser pulses at a first laser frequency; placing a fiber optical amplifier downstream from the fiber laser to receive the laser pulses and to amplify the laser pulses; coupling a segment of fiber to receive the amplified laser pulses from the fiber optical amplifier, the segment of fiber configured to exhibit normal optical dispersion as a nonlinear optical four-wave mixing medium; operating a seed laser to inject seed laser light at a second laser frequency different from the first laser frequency into the segment of fiber to coexist with the amplified laser pulses inside the segment of fiber to cause generation of a first output optical pulse at the first laser wavelength and a second output optical pulse at a third laser frequency generated via nonlinear four-wave mixing inside the segment of fiber; and directing the first output optical pulse and the second output optical pulse out of the segment of fiber into a target sample for Raman imaging that has a Raman-active vibration resonance equal to or near a difference between the first laser frequency and the third laser frequency to produce a Raman signal representing presence of the target sample.

In yet another aspect, a method for optical parametric oscillations is provided to include operating a fiber laser to produce laser pulses at a first laser frequency; placing a fiber optical amplifier downstream from the fiber laser to receive the laser pulses and to amplify the laser pulses; coupling a segment of fiber to receive the amplified laser pulses from the fiber optical amplifier, the segment of fiber configured to exhibit normal optical dispersion as a nonlinear optical four-wave mixing medium; operating a seed laser to inject seed laser light at a second laser frequency different from the first laser frequency into the segment of fiber to coexist with the amplified laser pulses inside the segment of fiber to cause generation of a first output optical pulse at the first laser wavelength and a second output optical pulse at a third laser frequency generated via nonlinear four-wave mixing inside the segment of fiber; and directing the first output optical pulse and the second output optical pulse out of the segment of fiber into an optical cavity containing a nonlinear optical material to produce a parametric optical oscillation.

These and other aspects, their implementations and specific examples are described in detail in the drawings, the description and the claims.

DETAILED DESCRIPTION

Figure 1:
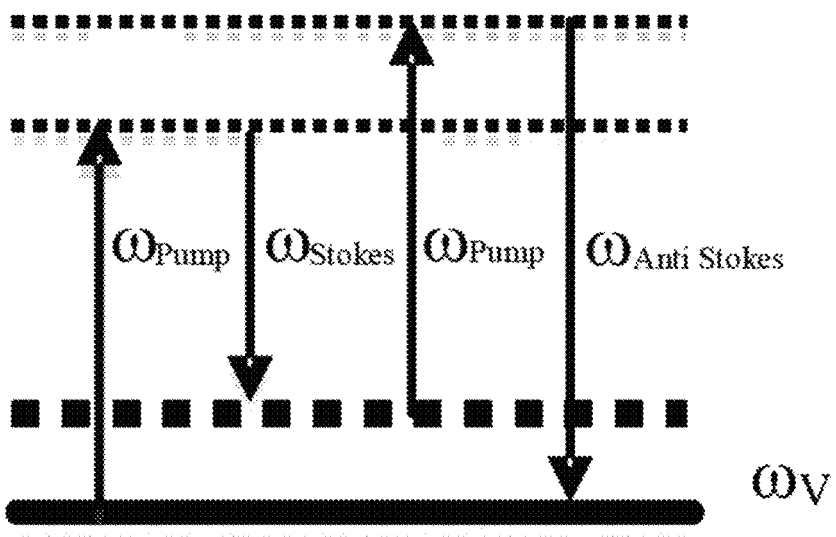
FIG. 1 shows an example of energy levels in a sample under Coherent anti-Stokes Raman scattering (CARS) microscopy.

Devices and techniques described in this document use nonlinear optical effects in optical fiber to generate coherent short optical pulses via nonlinear optical four wave mixing. The disclosed devices and techniques can be implemented to produce synchronized optical pulses at two different wavelengths to exhibit relatively narrow spectral widths with relatively short pulse durations. For example, such optical pulses may be configured to have a spectral width narrower than a relevant Raman spectral width of a sample or material for performing coherent Raman microscopic measurements. The pulse durations of such optical pulses can be in the picosecond range, e.g., 1 ps to around 10 ps in some implementations, to achieve sufficiently high pulse peak power for desired uses such as coherent anti-Stokes Raman scattering (CARS) microscopy, time-resolved material and chemical studies, non-linear microscopy, precision machining, and metrology. The wavelengths of such optical pulses can be tuned to desired wavelengths for various applications. The fiber-based implementations of the disclosed devices can be made compact and light weight with reliable operation when compared to bulky solid-state devices.

Devices and techniques described in this document are based on rare-earth ion doped fiber as an optical waveguide confine and guide light of different wavelengths involved in the nonlinear four wave mixing. Many components of such devices, including the pump laser, may be fiber based components to form compact configurations, and to provide simple and self aligned optical arrangement for aligning optical pump and signal beams. The optical spatial confinement and waveguiding for the signal and pump beams in fiber enable a relatively high gain per pass and good thermo-optical properties.

Notably, tight confinement of light into fiber leads to accumulation of large non-linear phase shifts. Unlike well-established understanding of nonlinear optical effects in various nonlinear crystals and other bulk optical materials that has been subject to over many decades of scientific research and technology development, the effects of the optical fiber nonlinearities to ultrashort pulse evolution in fiber are still evolving and facing various unknown effects or processes. When subject to anomalous dispersion in fiber, the pulse peak power of an optical pulse tends to be constrained by modulation instability and soliton formation.

At normal dispersion, new classes of chirped-pulse evolution such as similaritons and dissipative solitons emerge. Normal dispersion fiber can be configured or engineered to support large non-linear phase shifts and spectral broadening while avoiding wavebreaking. For example, the behavior of short optical pulses in the picosecond range, such as 1 picosecond to around 10 picoseconds, in normal dispersion photonic crystal fiber (PCF) can be different from the behavior of optical pulses with longer pulse durations such as tens of picoseconds to 100-200 picoseconds. Notably, nonlinear optical four-wave mixing in normal dispersion photonic crystal fiber (PCF) can be used to generate tunable picosecond pulses with relatively narrow spectral widths and high pulse peak power levels. To overcome spontaneous noise and pulse walk-off during proposition along the PCF fiber, optical seeding light for the idler wavelength can be used. This enables a two-color picosecond fiber laser in robust and integrable packages for various applications, including coherent anti-Stokes Raman scattering (CARS) microscopy for biomedical and other applications.

Raman spectroscopy is based on interaction between light and molecular vibrations, phonons or other excitations in an optical material to produce light with up or down shift in frequency. The shift in energy provides information about the vibrational modes in the material. A number of biologically-important substances (lipids, nucleic acids, sugars, e.g.) have characteristic vibrational spectra, which provide fingerprints for such substances for easy identification. Raman microscopic measurements are based on combination of microscopy with vibrational spectroscopy to generate images with chemical contrast. Coherent anti-Stokes Raman scattering (CARS) microscopy is a sensitive nonlinear technique that is noninvasive and offers chemical selectivity. In the CARS process light is coherently scattered from Raman-active vibrational resonances of a sample as illustrated by the energy diagram in a sample for CARS measurement in FIG. 1. FIG. 1 shows that optical pump and Stokes fields at $\omega_{Pump}$ and $\omega_{Stokes}$ are incident on a sample, respectively. When the frequency difference ($\omega_{Pump}$ and $\omega_{Stokes}$) is tuned to the frequency of a Raman-active molecular vibration $\omega_{Vibration}$, the resonantly-enhanced anti-Stokes signal is generated at frequency $\omega_{Anti\ Stokes}$. The coherent nature of the process enhances the signal. The resonantly-enhanced anti-Stokes signal at frequency $\omega_{Anti\ Stokes}$ allows high-speed imaging. One disadvantage of CARS is that the desired vibrationally-resonant signal is superposed on a "non-resonant" electronic contribution. The interference of these processes can distort the Raman signature and this distortion, in turn, can complicate image interpretation and limit the detection sensitivity. Stimulated Raman scattering (SRS) microscopy was developed, partly in response to this limitation of CARS. CARS and SRS microscopies are sometimes collectively referred to as coherent Raman microscopies (CRM). The same nonlinear susceptibility underlies Raman and multiphoton microscopies, so Raman also benefits from excitation localized to the focal plane.

The above CARS in various materials requires two-color picosecond pulses at for the optical pump field at $\omega_{Pump}$ and Stokes field at $\omega_{Stokes}$ and thus provides one example for the need of the devices and techniques described in this document. In some Raman applications, the light source of optical pulses for coherent Raman imaging can be configured to have some or all of the following characteristics:

The source needs to supply a synchronized pair of pulses, separated in frequency by the vibrational frequency of interest (typically 1600 to 3500 cm$^{-1}$). In some applications, the two pulses should have wavelengths in the range of 800 nm to 1300 nm to allow imaging based on vibrational modes with frequencies up to 3500 cm$^{-1}$, using wavelengths that can penetrate deep into tissue.

The pulse duration can be relatively short, e.g., in the range of 1-7 ps, with a transform-limited spectrum to match the linewidth of relevant molecular vibrations in the target materials or samples under measurements.

The pulse repetition rate of the pulses may be in the range of 10-100 MHz for video-rate imaging.

A relatively high peak power of approximately 1 kW or more may be desirable to achieve good signal-to-noise ratios at fast scan rates, e.g., a pulse energy of about 3 nJ for a 3-ps pulse and an average power of 300 mW for a 100-MHz repetition rate.

Fluctuations in the power, pulse duration, and timing should be small to increase sensitivity.

The source can supply high-quality beams with good pointing stability.

The source should be compact and robust, with turn-key operation and little maintenance.

It can be technically challenging to meet the above requirements. In various CARS imaging applications, synchronized picosecond Ti:sapphire lasers have been used as the choice of light sources with an optical wavelength tuning range of 700 nm-1000 nm. Solid-state lasers, e.g., using a crystalline Nd gain element, may also be used in CARS by synchronously pumping an optical parametric oscillator (OPO) that generates the desired two colors for CARS. These solid-state systems tend to be expensive (e.g., over $200,000 per instrument), and physically large, and may require special maintenance and vibration isolation for sufficient operation stability. A fiber laser source based on the described four wave mixing designs in this document can be configured to offer one or more practical advantages over solid-state light sources, including using the fiber waveguide medium to avoid the need for alignment and ensures good spatial mode quality, using the scalable proper of the fiber design to achieve high average powers by increasing the length of the nonlinear fiber, coiling the fiber to achieve compact device configurations and reducing manufacturing costs by using low-priced commercial optical components fabricated based on telecommunications components for fiber networks. Thus, fiber-based sources of pulses for coherent Raman microscopies would be attractive. A fiber laser for Raman microspectroscopy can be configured to produce synchronized optical pulses and structured to be environmentally-stable. In some bioimaging applications, a pair of synchronized picosecond pulses can be advantageously used for imaging. The techniques and devices described here based on optical four wave mixing can be used in ways that meet the above and other requirements.

Optical four-wave-mixing (FWM) tends to be the dominant wave mixing mechanism in glass fibers. The FWM gain is determined by the dispersion profile $\beta(\omega)$ and the nonlinear phase shift $\gamma P_0$ of the fiber:

$$g = \sqrt{(\gamma P_0)^2 - (\kappa/2)^2}$$

$$\kappa = 2\gamma P_0 + 2\sum_{i=1}^{\infty} \frac{\beta_{2m}}{(2m)!} \Omega^{2m}$$

If the fiber dispersion is anomalous, the balance of $\beta_2<0$ and $\gamma P_0$ dominates the phase-matching. This anomalous dispersion in fiber can cause broadband, closely-spaced modulation-instability sidebands. If the fiber dispersion is normal, the phase-matching is dominated by higher-order dispersion. Under the normal dispersion condition in fiber, the FWM sidebands generated in the fiber are narrowband, and appear at large frequency shifts. For many applications for short laser pulses such as CARS, this normal dispersion condition in fiber is a desirable regime for picosecond pulse conversion.

The specific implementations described here use photonic crystal fiber (PCF) as examples of normal dispersion fiber for the FWM process. The photonic crystal fiber (PCF) technology can be used to tune the dispersion and thus provide the desired phase-matching. In addition to PCF fiber, other normal dispersion fiber may also be used to implement the described technology.

Figure 2A:
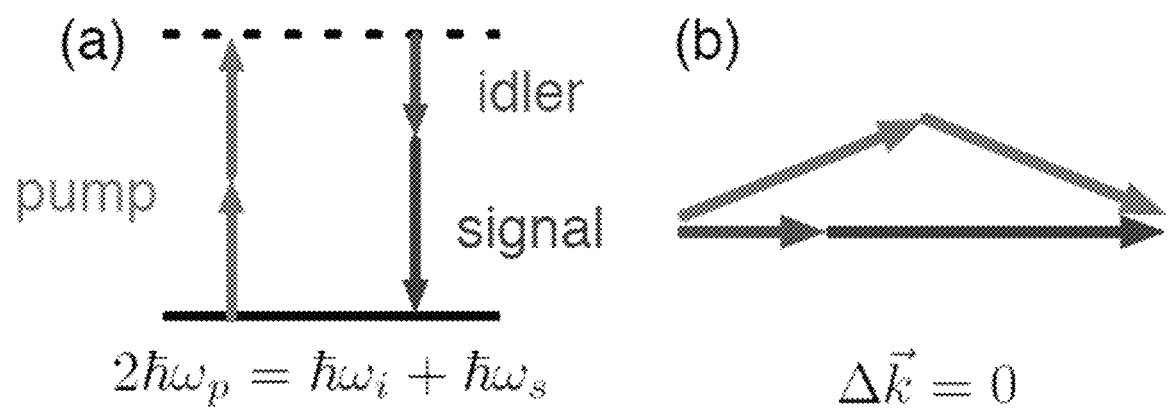
FIG. 2A shows the energy conversation and phase matching in four wave mixing.

Four-wave mixing in fiber, such as photonic crystal fiber (PCF), is a non-linear process resulting from frequency mixing by the third-order non-linear response of the fiber material in which three waves mix to generate a fourth wave at a new frequency. As illustrated in FIG. 2A, both energy conservation and phase matching must be satisfied:

$\omega_1 + \omega_2 = \omega_3 + \omega_4$ (energy conservation)

$\Delta k = k_1 + k_2 - k_3 - k_4 = 0$ (phase matching)

In the exemplary devices described in this document, the degenerate FWM with two pumps at the same pump frequency $\omega_1 = \omega_2 = \omega_p$ are used. Two pump photons mix to generate a signal beam at signal beam frequency of $\omega_s$ and an idler beam at the idler optical frequency of $\omega_i$:

$2\omega_p = \omega_s + \omega_i$ (energy conservation)

$\Delta k = 2k_p - k_s - k_i = 0$ (phase matching)

In CARS applications as illustrated in FIG. 1, the FWM-generated signal beam at the optical frequency of ωs from the above FWM process can be used as the pump beam in CARS and the FWM-generated idler beam at the idler optical frequency of ωi or the pump beam at the pump optical frequency of ωp can be used as the Stokes optical beam in CARS.

The disclosed technology in this document uses the above FWM process to convert relatively short laser pump pulses, e.g., pulses with a pulse duration in the picosecond range (such as 1 ps to 10 ps) to FWM-generated pulses with large frequency shifts from the pump frequency. FWM in photonic crystal fiber (PCF) has been used to convert 100-200 ps pulses to large frequency shifts with significantly large deviations from the transform limit and significant fluctuations in the converted pulses. These properties of FWM-generated pulses with long durations are detrimental to CARS imaging. Transform-limited pulses with spectra that are within the vibrational linewidth (~10 cm$^{-1}$ in various materials typically used for CARS imaging) would be desirable. For the desired few-picosecond pulses, interaction lengths are only tens of centimeters due to group-velocity mismatch (GVM), which limits FWM conversion. As a result of these and other issues, CARS microscopy of biological samples has not been demonstrated with a fiber-FWM source.

The devices and techniques described in this document based on the FWM in FIG. 2A can be designed to be suitable for CARS and other applications. Various features in the disclosed devices and techniques are described below.

Figure 2B:
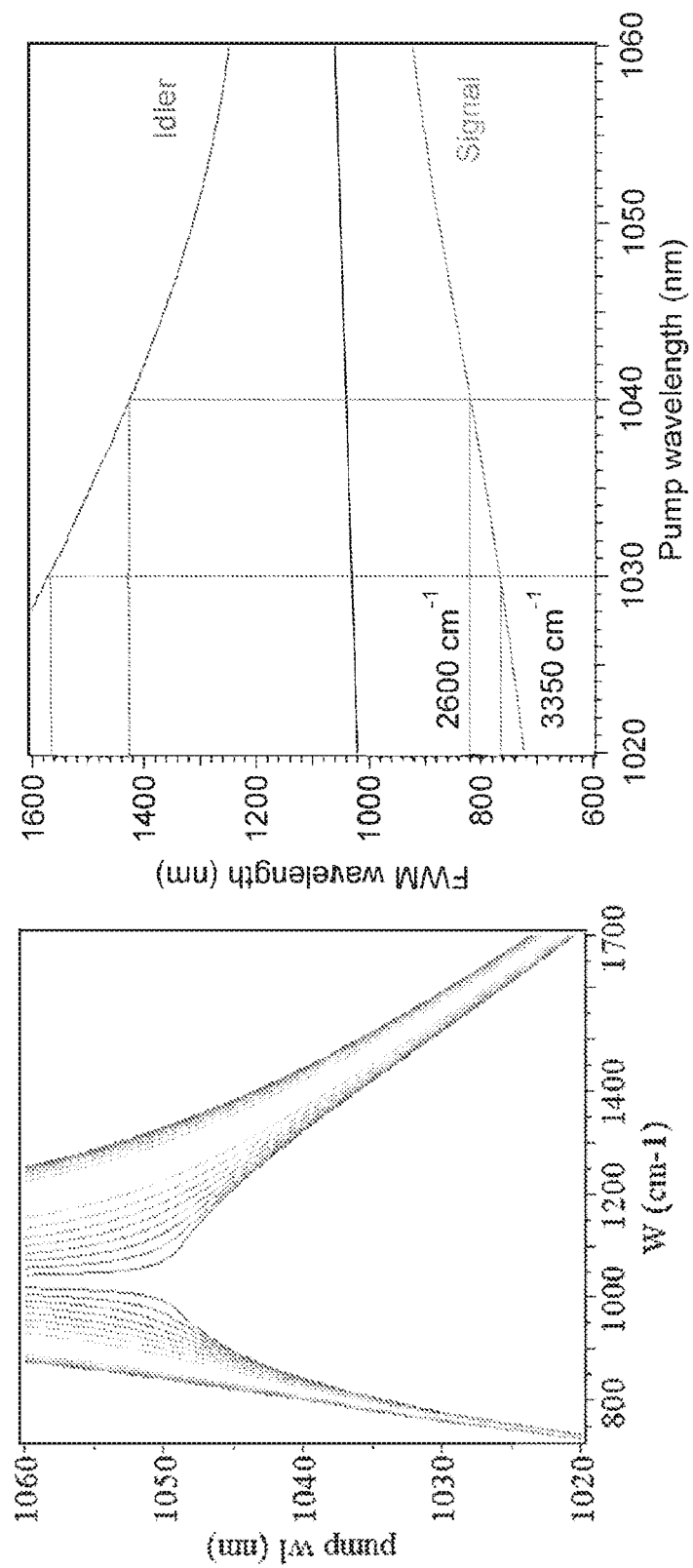
FIGS. 2B, 2C, 2D and 3 show data for various properties of four wave mixing signals in nonlinear fiber with normal dispersion.

The nonlinear fiber used in the disclosed devices is normal dispersion fiber to achieve spectrally narrow FWM sidebands with large frequency shifts that are desirable in CARS and other applications. The simulation under the phase-matching of the FWM process in FIG. 2B shows widely spaced and narrow bands. The positions of such bands can be controlled by tailoring the dispersion of the PCF, mainly its zero-dispersion wavelength (ZDW). The right-hand-side figure in FIG. 2B shows the phase-matching diagram for an endlessly single-mode PCF with a ZDW of 1051 nm. The dispersion coefficients $\beta_n$ at 1036 nm are 1.48 fs$^2$/mm, 59.5 fs$^3$/mm, −69.5 fs$^4$/mm, 136 fs$^5$/mm and −180 fs$^6$/mm. The cw pump power matches the expected pulse peak power. This example shows that a pump laser tunable from 1030 nm to 1040 nm can be shifted by FWM in PCF to wavelengths between 770 nm and 820 nm with narrow bandwidths.

The wide frequency spacing in the FWM shown in FIG. 2B indicates that the FWM in such a normal dispersion fiber can occur by only injecting the pump beam at the pump frequency $\omega_p$ alone into the normal dispersion fiber, without injecting any light at either the idler beam frequency $\omega_i$ or the signal beam frequency $\omega_s$. Under this operation, with sufficient power in the pump beam at the pump frequency $\omega_p$, the signal light at the signal beam frequency $\omega_s$ and the idler light at the idler beam frequency $\omega_i$ can grow from low-level noise in the fiber due to, e.g., quantum noise or thermal noise in the fiber. This process can significantly hinder both the efficiency and coherence of the FWM process. Therefore, a seed optical beam with a narrow spectral width, low noise at the idler beam frequency $\omega_i$ (a seeded idler beam) or at the signal beam frequency $\omega_s$ (a seeded signal beam) can be used to initiate the idler or the signal for enhancing the efficiency of the FWM process and the coherence of the generated signal.

To understand the FWM process in the pulsed regime, numerical simulations were performed to account for higher order dispersion, spontaneous and stimulated Raman scattering, self-steepening, and input shot noise. With only the input picosecond pump and unseeded sidebands, the process initially grows from spontaneous noise.

Figure 2C:
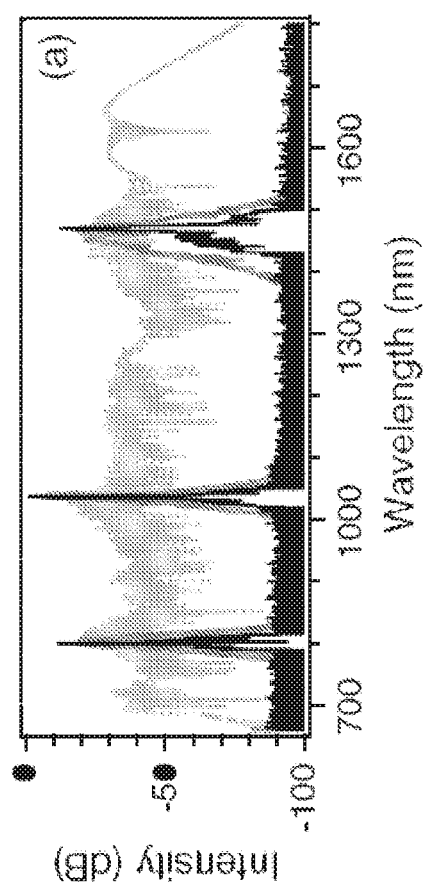

FIG. 2C shows an exemplary spectrum of a FWM measurement with injection of pump light only with any seeding light. The measurement was Obtained after the signal field near 800 nm reaches 3.1 nJ of pulse energy (which is a typical every level required for a CARS source). Broad (e.g., a spectral width greater than 10 nm), randomly fluctuating signal and idler bands developed from noise. The measurement shows that the signal energy saturates below 6 nJ as supercontinuum generation takes over due to non-phase-matched processes dominating beyond the GVM length. Therefore, the GVM adversely limits the FWM process.

Figure 2D:
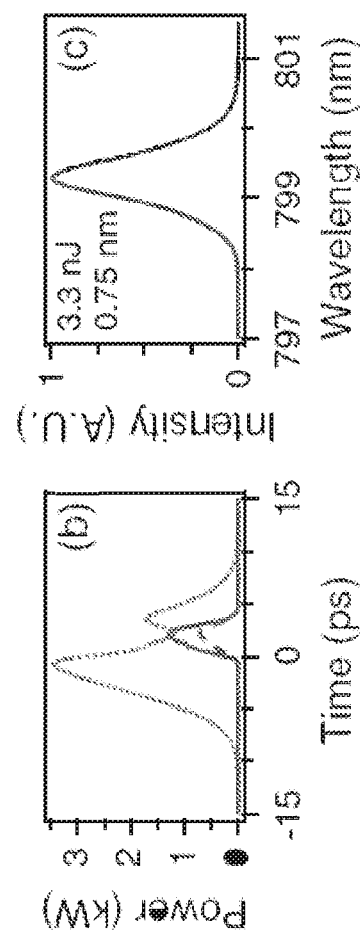

Based on the above recognition, devices and techniques disclosed in this document use seeding the FWM process, e.g., injecting a seeding idler beam, to allow the FWM fields to build up from high quality pump and seeding beams before the GVM separates these signals. Such seeding for initiating the FWM process can be used to reduce fluctuations in PCF to counter the adverse impact of GVM. Measurements on seeded FWM were tested by injecting cw light at the idler frequency in FWM. FIG. 2C further shows an example of the measured spectrum in a seeded FWM in PCF after 30 cm of propagation as a comparison with the unseeded FWM results at similar energies. FIG. 2D shows details of the FWM measurements in the seeded FWM in PCT. Significant spectral narrowing is achieved, and the conversion efficiency is above 10%. Further conversion is limited by coherent energy exchange between fields, which generates structured pulses.

Hence, the above seeding the idler light to the FWM enables the FWM generation to produce optical pulses with a narrow spectral width, avoid undesired increase in the pulse duration, to achieve good optical coherence and a high conversion efficiency and to achieve a high quality beam profile.

In the regimes of short optically pulses, e.g., 3-7 ps, Raman microscopy can be hindered by different group velocities of the pump, signal and idler pulses in the fiber. The pump, signal and idler pulses move away from one another as they propagate in the fiber. As a consequence, the FWM interaction becomes weak, and such separation of pump, signal and idler pulses can lead to optical effects that occur with a single pulse, such as continuum generation and stimulated Raman scattering. These effects can produce broad spectra that degrade the performance for Raman microscopy. Notably, with few-picosecond pulses, the pump-signal "walkoff" can arise from the group-velocity mismatch (GVM) and can be fast enough to inhibit efficient spontaneous conversion. In a short enough piece of fiber, the different-color pulses do not walk off from each other, but the conversion can be inefficient owing to the reduced interaction length.

One aspect of this document is construction of a compact and efficient fiber source of synchronized picosecond pulses for Raman microscopy. This fiber source can include a picosecond fiber laser to produce optical pulses, a fiber amplifier that amplifies the optical pulses, and a segment of fiber with normal dispersion for the FWM process. A seed laser is coupled to provide seed light, along with the pump light, to the segment fiber for the FWM process. In some implementations, fibers can all be spliced together, so that the light pulses do not leave the waveguide medium until reaching the output port of the device. This fiber source can be used to provide a fiber-based frequency-conversion stage that produces the narrowband picosecond-duration pulses for Raman microscopy and other applications.

Seeding of parametric processes increases efficiency and reduces fluctuations. Seeding of the FWM process can be implemented to counter the effects of group-velocity mismatch by allowing the signal and idler fields to build up before the pulses separate temporally. This use of a seed field to counter the effects of group-velocity mismatch in a nonlinear-optical process can facilitate desired FWM process to develop and to dominate the undesirable continuum generation and stimulated Raman scattering, which produce undesired broadband spectra.

Figure 3:
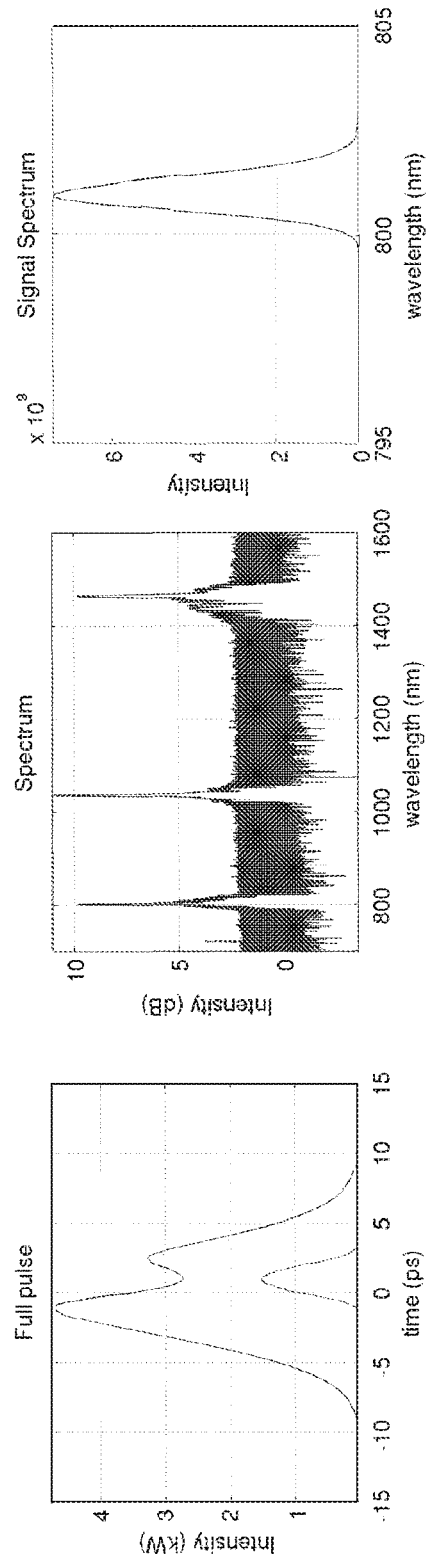

FIG. 3 shows additional numerical simulations of pulse propagation in fiber that confirm the validity of the seeding design. The dispersion parameters of a sample PCF used in the simulations are as follows. A 1030-nm pump pulse with 7 ps duration and peak power of 5 kW is converted to signal light near 800 nm with efficiency above 10% (FIG. 3) after propagation through 30 cm of PCF. The overall spectrum (middle panel of FIG. 3) shows the production of widely-spaced but narrowband spectral regions, and the left and right panels in FIG. 3 demonstrate the generation of approximately 2-ps pulses with bandwidth near 1 nm. The signal and idler pulses are shorter than the input pump pulse (left panel of FIG. 3). The simulations also show that a few milliwatts of continuous-wave power at the signal or idler wavelength is enough to overcome the quantum noise background. The pump pulse then gates the continuous-wave field and amplifies the short pulse.

Based on the above and other considerations, in one implementation, an optical fiber source for producing optical pulses can be designed to include a fiber laser to produce laser pulses at a first laser wavelength; a fiber optical amplifier placed downstream from the fiber laser to receive the laser pulses and to amplify the laser pulses; a segment of fiber coupled to receive the amplified laser pulses from the fiber optical amplifier and configured to exhibit normal optical dispersion as a nonlinear optical four-wave mixing medium; and a seed laser coupled to the segment of fiber to inject seed laser light at a second laser wavelength different from the first laser wavelength into the segment of fiber to coexist with the amplified laser pulses inside the segment of fiber to cause generation of a first optical pulse at the first laser wavelength and a second optical pulse at a third laser wavelength generated via nonlinear four-wave mixing inside the segment of fiber.

Figure 4:
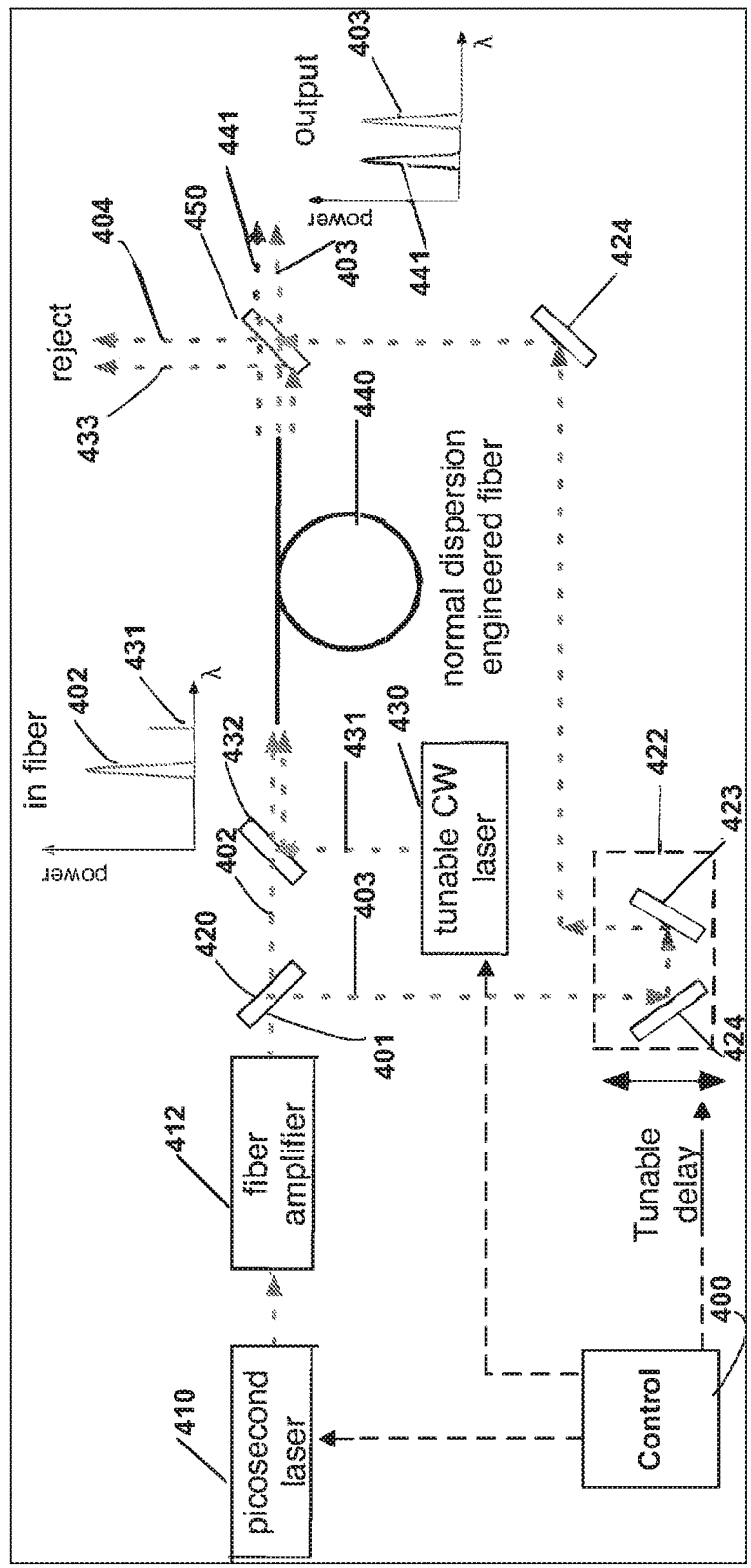
FIG. 4 shows an example of a FWM-based optical device for pulse generation.

FIG. 4 shows an example of such a fiber source. A normal dispersion fiber segment 440 is used as the FWM nonlinear medium. A picosecond pulse laser 410 is provided to generate pump pulses at the pump wavelength in FIG. 2A with a pulse duration in the picosecond range, e.g., 1 ps to 10 ps in some implementations. The laser 410 can be, e.g., a fiber laser such as a soliton fiber laser that generates 7-ps pulses at 1030 nm wavelength. An optical amplifier 412 is provided to amplify the laser pulses from the laser 410 as pump laser pulses 401. The amplifier 412 can be implemented in various configurations by based on a fiber amplifier or other optical amplification designs. For example, the amplifier 412 can include a core-pumped single-mode Yb-doped fiber amplifier to amplify the pulses to approximately 1 nJ energy per pulse. The pulses may be further amplified, using divided-pulse amplification to avoid nonlinear distortion of the pulses. The divided-pulse amplifier for the divided-pulse amplification can be part of the amplifier 412 and may include, for example, a sequence of four $YVO_4$ crystals, which allows amplification to pulse energy (peak power), e.g., at least 70 nJ (10 kW), without significant distortion. A pump optical beam splitter 420 is provided at the output of the amplifier 412 to split the pump beam 401 into a bypass pump beam 403 and a pump beam 402. The pump beam 402 is used to pump the fiber 440 for the FWM.

The device in FIG. 4 includes a seed laser 430 that is optically coupled to inject seed laser light 431 at a second laser wavelength different from the pump wavelength into the segment of fiber 440 along with the pump light. The seed light 431 can be at the optical idler beam frequency or the signal beam frequency in FIG. 2A. In the example shown, the seed light 431 can be at the optical idler beam frequency. A beam combiner, e.g., a dichroic beam mirror that transmits the pump light 402 while reflecting the seed light 431, is provided to combine the pump beam 402 containing the amplified laser pulses and the seed light 431 together as input beams into the fiber 440 for FWM. The seed laser 430 can be a continuous-wave (CW) laser, e.g., a tunable CW laser. The wavelength of the seed light 431 can be selected, e.g., 1545 nm in the example shown or at other wavelengths depending on the need of a specific application. The amplified pulses 402 and continuous-wave seed light 431 are coupled into the PCF 440 for the FWM process. Prototype devices based on FIG. 4 were built by using PCF to generate a FWM signal at 770 nm and an idler signal at 1545 nm with the input pulses from the divided-pulse amplifier. This design allows for convenient generation of the seed pulse, with a semiconductor diode laser and an erbium fiber amplifier. The seed laser 430 can be a low power CW laser with a power significantly lower than the pump beam 402, e.g., a laser of a few milliwatts may be adequate in some applications.

The optical output of the normal dispersion fiber segment 440 includes light at 3 wavelengths: a first output beam at the pump wavelength, a second output beam at the idler wavelength and a third output beam at the FWM signal wavelength. The second output beam at the idler wavelength and the third output beam at the FWM signal wavelength are generated by conversion of the pump energy via the FWM process and contain optical pulses with relatively short pulse durations and narrow spectral widths. The output beam at the pump wavelength is mainly residual pump light that is left over from the conversion of energy at the pump wavelength into the energy at the signal and idler wavelength in the FWM process. The output beam at the pump wavelength has a broadened spectral width in comparison with the original pump pulses prior to entry of the PCF 440.

The output design of the device in FIG. 4 can be used to output either one or both of the third output beam at the FWM signal wavelength and the second output beam at the idler wavelength. In this example, however, the output design is configured to separate the third output beam at the FWM signal wavelength from the first output beam at the pump wavelength and the second output beam at the idler wavelength so that the bypass pump beam 403 at the pump wavelength and the third output beam at the FWM signal wavelength are combined as the two-color output of the device. An output device or module 450 is provided in FIG. 4, e.g., a wavelength selective beam splitter or mirror, to reflect the first output beam at the pump wavelength and the second output beam at the idler wavelength while transmitting the third output beam at the FWM signal wavelength. The bypass pump beam 403 is directed to the output device and is reflected by the output device to combine with the transmitted the third output beam at the FWM signal wavelength. The bypass pump beam 403 does not go through the PCF 440 and thus retains the spectral width and pulse duration of the pump beam. Due to the spectral broadening in the PCF output beam at the pump wavelength, the bypass pump beam 403 is a higher quality beam than the PCF output beam at the pump wavelength.

As shown in FIG. 4, a variable delay loop is provided to guide the bypass pump beam 403 and to combine with the third output beam at the FWM signal wavelength of the PCF 440 for synchronization. The variable delay loop can be operated to adjust the amount of optical delay in the bypass pump beam 403 at the device output port so that the optical pulses in the bypass pump beam 403 and the optical pulses in the third output beam at the FWM signal wavelength are synchronized in time. One way for achieving the synchronization is to direct the two-color output in FIG. 2 to a CARS measurement setup and to adjust the delay in the variable delay loop to maximize the signal amplitude the CARS signal. The variable delay loop can be implemented in various configurations and the example in FIG. 4 uses a variable delay module 422 with one or more movable mirrors 424 and 423 whose position can be adjusted to change the overall optical path length of the variable delay loop.

Figure 5:
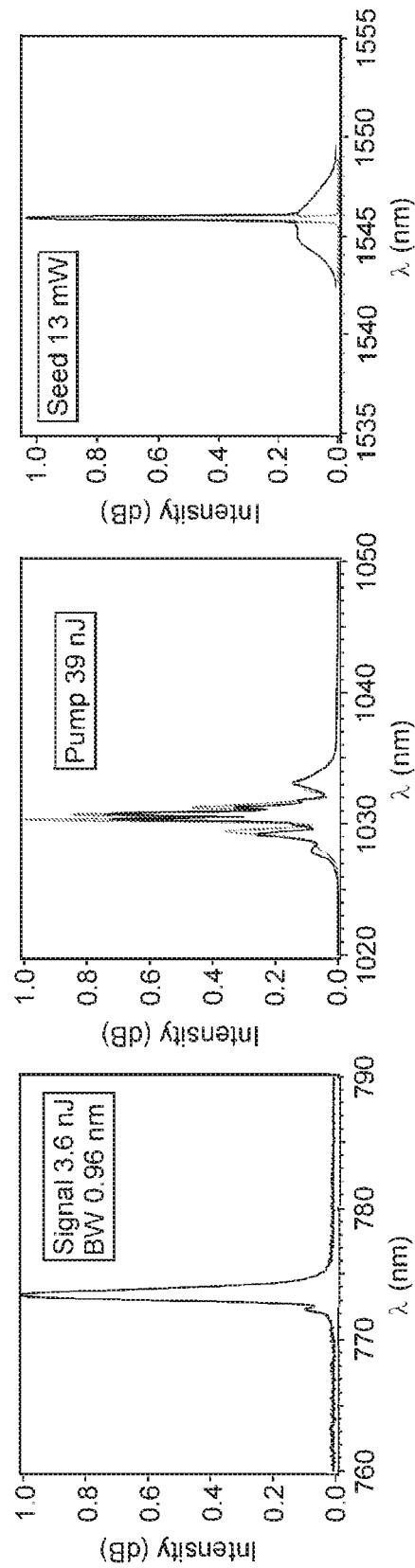
FIGS. 5, 6 and 7 show properties of the device in FIG. 4.

In operation, the polarizations of the seed light 431 and the pump beam 402 are identical to each other in order to cause the FWM interaction. In a device based on the design in FIG. 4, various optical polarization control elements are provided to ensure optical polarizations of the beams at various locations are proper. Upon adjustment of the seed wavelength and pump polarizations, FWM is observed and signal conversion with close to 10% efficiency occurs for PCFs 20 to 30 cm in length (FIG. 5). This yields 3-nJ signal pulses at 774 nm. The signal pulse is 1.5 ps in duration (FIG. 6), near the transform limit of 1 ps. A small secondary pulse was sometimes visible 20 ps away from the main pulse in various test runs. Depending on the exact tuning of pump power and seed wavelength, this signal carried between 0.1% to 1% of the energy. This secondary pulse may arise from residual features in the output of the divided-pulse amplifier used in the test runs. Without the seed light, the FWM signal and idler are 1000 to 10,000 times weaker than the FWM signal generated with the seed. This control measurement demonstrates that the seed light can be used for efficient generation of the narrowband signal and idler pulses.

Figure 6:
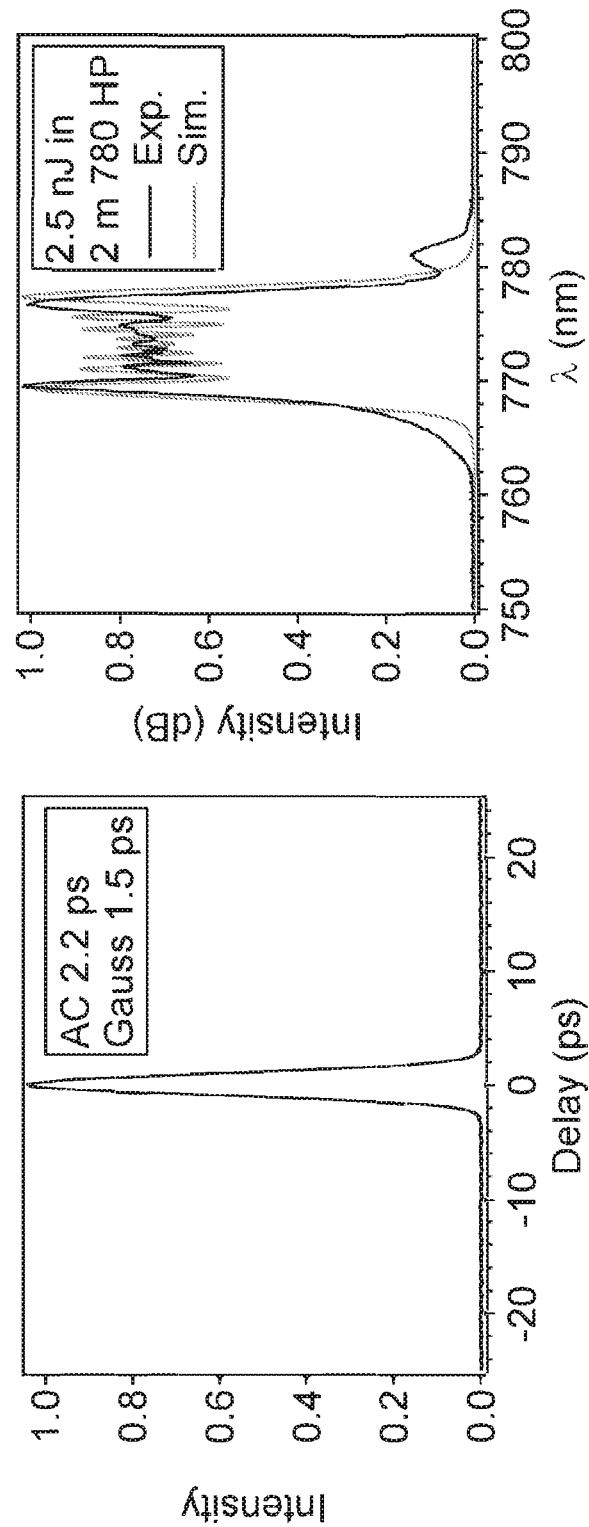

In the test runs, the peak power of the signal pulse was verified by launching the signal pulse into a 2 m length of single-mode fiber (Nufem 780HP). With 2.5 nJ injected, the spectrum broadens to about 11 nm width. Simulations using a Gaussian pulse with similar duration, energy and bandwidth match the observed broadening (FIG. 6). This confirms the coherence and quality of the pulses generated by seeded FWM.

Figure 7:
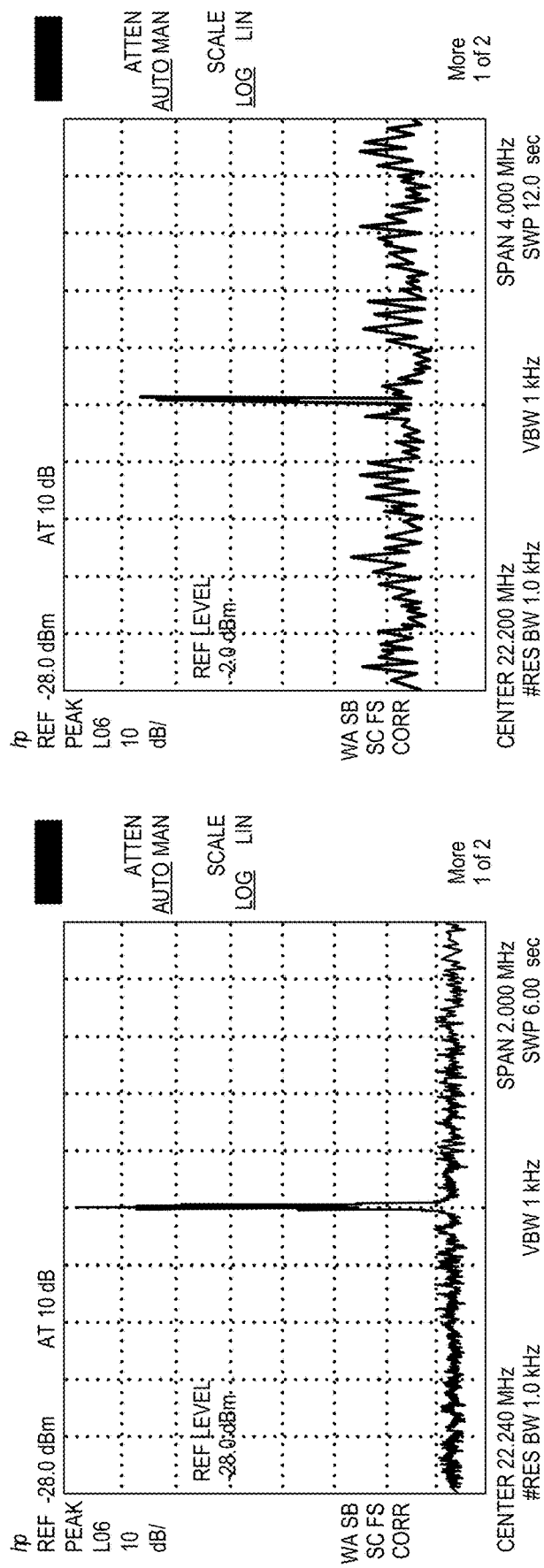

Pulse-to-pulse stability is desirable for sensitive imaging and other applications. In some imaging applications, fluctuations of about 1% in the signal pulse energy can be observed with a fast photodiode. The radio-frequency (RF) spectrum reveals a white noise background about 70 dB below the fundamental harmonic of the pulse train (left panel of FIG. 7). Considering the time scale of the fluctuations, the fluctuations may be due to fluctuations in the continuous-wave seed field. To test this hypothesis, the system was seeded with a continuous-wave Er fiber laser. The fiber laser has a linewidth of about 0.1 nm, compared to less than 0.05 nm for the diode laser and amplifier system discussed above. Greater fluctuations are expected due to the shorter coherence time for the fiber laser. The noise background does increase as expected (right panel of FIG. 7): the noise is only 40 dB below the main peak. These results imply that it may be possible to further enhance the stability of the FWM source by use of a single-frequency diode laser as the seed. On the other hand, the 1% fluctuations observed above are already adequate for high-quality imaging.

Therefore, a fiber source can be constructed based on the above seeding design to produce synchronized, energetic, narrowband, picosecond optical pulses appropriate for coherent Raman microscopies. As an example of how the source would be used, the signal pulse at 770 nm and the residual pump pulse at 1030 nm would be directed into the Raman microscope as the so-called "pump" and "Stokes" waves in the Raman process. FIG. 5 shows that the residual pump spectrum can be distorted by self-phase modulation as it traverses the PCF. Thus, in one embodiment, part of the 1030-nm pulse would be split off as the bypass pump beam 403 before the FWM fiber to avoid this distortion. This is indicated in FIG. 4 where the undistorted bypass pump beam 403 is used to replace the residual pump output of the PCF as the two-color output for the device.

The frequency difference between the unconverted pump light and the signal wavelength can be varied to cover several of the biologically-important vibrational modes. For example, a fiber laser tunable between 1030 and 1040 nm can be used to excite modes with frequencies between 2600 and 3350 $cm^{-1}$. This tenability function of the disclosed fiber source can be versatile, capable of application to a variety of biological imaging situations.

More specifically, in the devices and techniques described in this document based on the FWM in FIG. 2A, the FWM-generated signal beam at the optical frequency of $\omega_s$ can be tuned over a wide wavelength range by tuning the pump beam wavelength. For example, with some commercially-available PCF fiber products, tuning the FWM-generated signal beam over the important spectral range 2600 cm$^{-1}$ to 3300 cm$^{-1}$ for various applications is possible by tuning the pump wavelength for FWM from 1030 nm to 1040 nm. This is illustrated by the computation results for a normal dispersion PCF under a pump peak power of 5 KW in FIG. 2B. Modest variation of the pump wavelength can be used to yield useful variation of the signal wavelength. Notably, in an implementation where both pump and idler beams are sent into the nonlinear fiber (e.g., PCF) for the FWM, in addition to tuning the pump wavelength to tune the wavelength or frequency of the FWM-generated signal beam, the wavelength of the injected idler beam can also be tuned to tune the wavelength or frequency of the FWM-generated signal beam. The tuning of the pump beam wavelength provides a wide range, coarse tuning of the wavelength of the FWM-generated signal beam while tuning of the idler beam wavelength provides a smaller and fine tuning of the wavelength of the FWM-generated signal beam. In implementations, the tuning of the idler beam wavelength can be used either alone without tuning the pump beam wavelength or in combination with tuning of the pump beam wavelength. In PCF fibers, the tuning of the idler beam wavelength can tune the wavelength of the FWM-generated signal beam over a few nanometers, e.g., 1 nm to 2 nm. This frequency tuning of the FWM-generated signal beam in the disclosed devices enables versatile applications over different wavelengths.

Referring to FIG. 4, a control 400 is illustrated for provide the FWM signal tuning operation. The control 400 as a laser tuning controller can be coupled to the pump laser module 410 or the seed laser 430 and is configured to tune a wavelength of the pump laser module 410 or the seed laser 430 to achieve tuning of the signal wavelength of the four wave mixing signal 441. As described above, tuning the pump laser 410 allows for a wide tuning range and tuning the idler wavelength of the seed laser 430 provides fine tuning. The laser tuning controller 400 can also be coupled to both the pump laser module 410 and the seed laser 430 to tune a wavelength of the pump laser module to provide the wide tuning of the signal wavelength of the four wave mixing signal 441, and to control a wavelength of the seed laser 430 to achieve a fine tuning of the signal wavelength of the four wave mixing signal 441. The laser tuning controller 400 may also be used to control the delay in the delay path for by the bypass pump beam 403.

Figure 8:
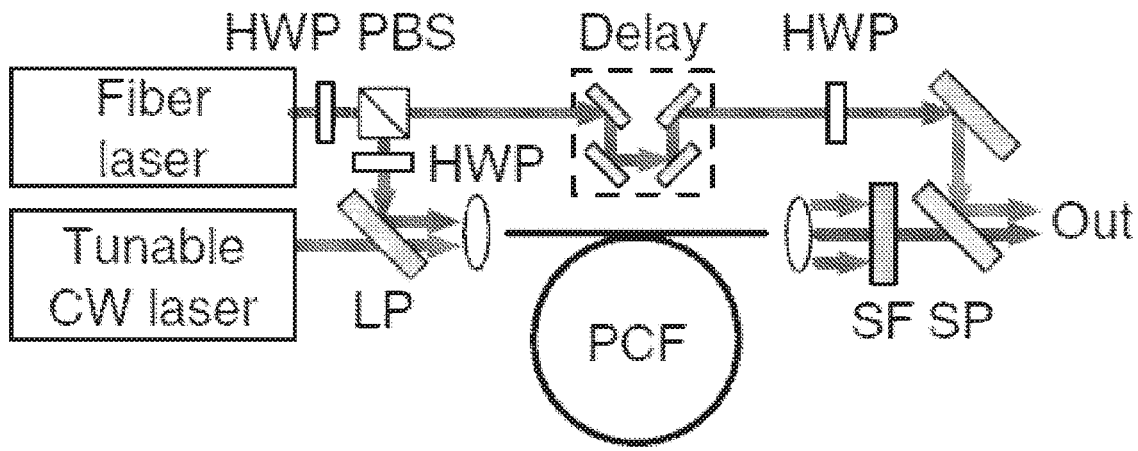
FIGS. 8 and 9 show another example of a device based on the design in FIG. 4 and measurements of the device.
Figure 9:
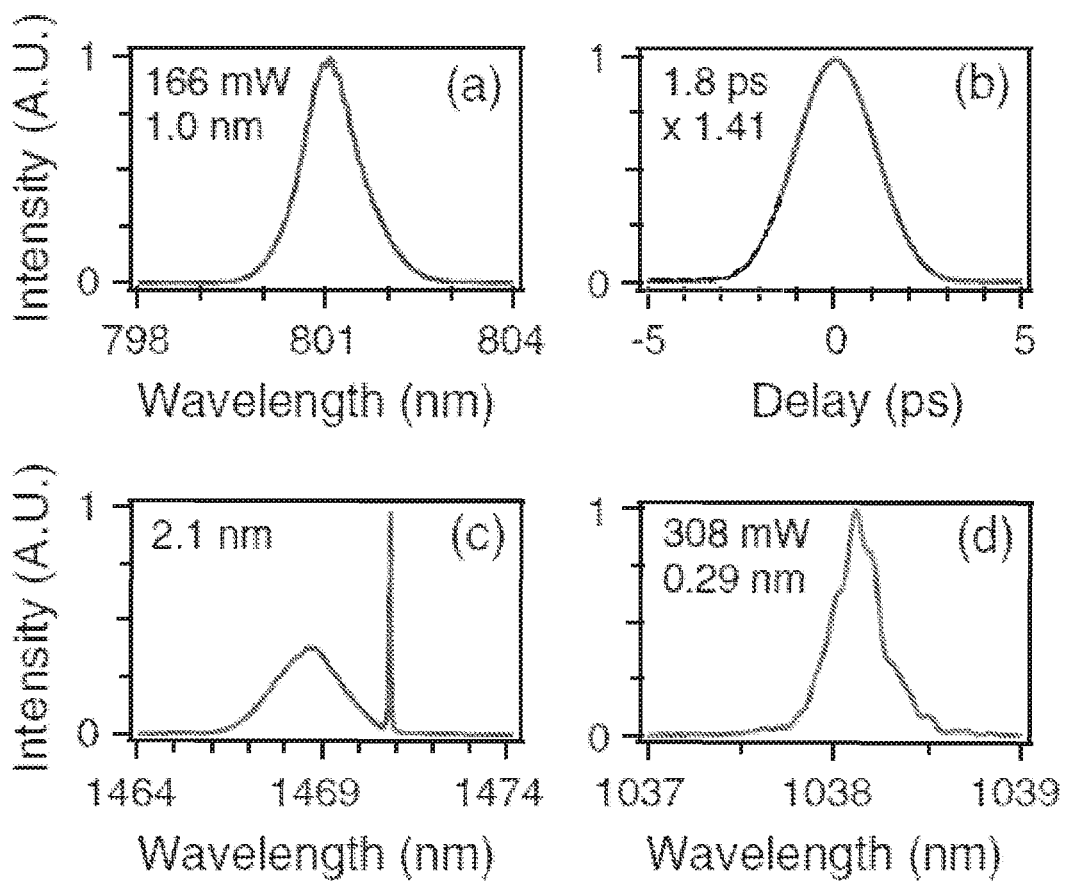

FIGS. 8 and 9 show a specific example of a device based on the design in FIG. 4. In FIG. 8, a tunable Yb-doped fiber laser (modified TOPTICA PicoFYb) is coupled to a divided-pulse amplifier based on a 10 μm core diameter double-clad Yb-doped fiber. This produces 2.5 W of pulses with 7.7 ps duration at the 54 MHz repetition rate. This is combined with a fiber-coupled diode laser tunable from 1400 nm to 1490 nm and providing up to 30 mW (TOPTICA DL pro). The polarization-matched beams are coupled into an endlessly single-mode PCF with normal dispersion for the FWM process. Filters block the anti-Stokes light generated by mixing of the signal and pump in the PCF. A fraction of the 1 μm pulses is picked off before the PCF and combined with the polarization-matched signal at the microscope. Various polarization control elements, such as half wave plates (HWPs), polarization beam splitter (PBS), and linear polarizer (LP), are provided in FIG. 8 to manipulate the optical polarization to ensure the proper beam routing, proper operation at the PCF for FWM and the proper output.

FIG. 9 shows experimental results with 30 cm of PCF. Pump pulses of 1.6 W are coupled into the PCF. The idler is seeded with 5.1 mW at 1471 nm. The generated signal pulses have 166 mW of average power and a duration of 1.8 ps, while 308 mW of pump pulses are picked off. The performance is similar to solid-state systems. Higher powers or longer fibers yield higher signal energies and structured spectra. The frequency difference of 2850 cm$^{-1}$ corresponds to the CH$_2$ stretching vibration. With the tuning range of the diode, we achieved similar performance for frequency shifts of 2650 and 2950 cm$^{-1}$. By use of a similar fiber amplifier centered at 1031 nm and an amplified diode laser tuned to 1546 nm, we generated a signal wavelength of 774 nm, corresponding to a Raman shift of 3200 cm$^{-1}$. Coarse tuning can be accomplished by changing the pump wavelength, while fine tuning over 1 to 2 nm can be done by tuning the seed. No realignment is required.

The FWM signal and picked-off pump are coupled into a laser-scanning microscope (customized Zeiss LSM 510) and focused using a 40× water-immersion objective with NA of 1.1. We detect the forward-generated CARS signal with a nondescanned photomultiplier tube. The total power delivered to the samples is about 60 mW. CARS images at a 2850 cm$^{-1}$ shift from a mouse ear and reveal the subcellular lipid distribution in a sebaceous gland 40 μm deep in tissue. FIG. 5(c) shows a mouse brain section with the myelin sheath wrapped around the axons.

The above fiber source can be used for various applications. For example, the seeded FWM process for generating narrowband picosecond pulses described here can be used in an optical parametric oscillator with a feedback which is different from the single-pass parametric generation scheme described above. To implement a parametric oscillator, the FWM fiber can be incorporated into an optical feedback mechanism, e.g., an optical cavity or resonator, that feeds back some of the output to the input. In some implementations, this optical feedback (e.g., a cavity) may include a segment of fiber that connects the output to the input to form a fiber ring resonator, with provision of an output coupler to provide an optical output. In such an optical parametric oscillator, the seeding of the process may not be necessary in some applications, thus eliminating the need for the seed light source and reducing the cost of the source. The optical cavity length can be matched closely to the repetition rate of the fiber amplifier.

Figure 10:
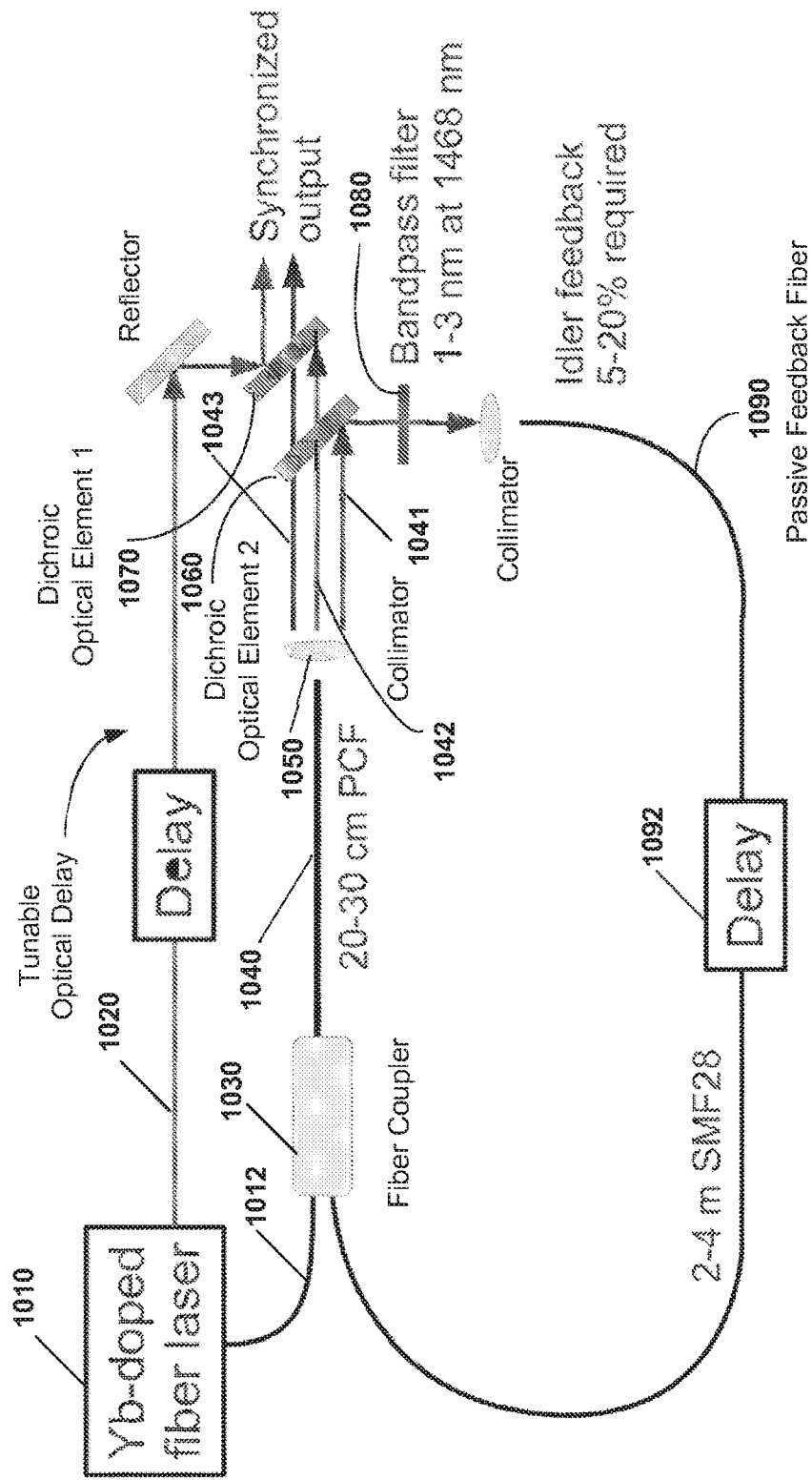
FIG. 10 shows an example of an optical parametric oscillator based on FWM.

FIG. 10 shows an example of a fiber-feedback picosecond optical parametric oscillator for coherent Raman microscopy and other applications. A pump laser 1010 is provided to generate a pump beam with pump pulses. The laser 1010 may be in various configurations, e.g., a high-power picosecond fiber laser system with an output power of 1-2 W at a 50-80 MHz repetition rate and a pulse duration around 7 ps. The pump pulses are coupled into a dispersion-engineered PCF 1040 with normal dispersion to cause FWM in the PCF 1040 which generates a blue-shifted FWM signal 1043 and a red-shifted idler signal 1041. The output of the PCF also includes a signal 1042 at the pump frequency which includes the residual pump from the input. The output module in FIG. 10 is designed to output the FWM signal 1043 along with a synchronized bypass pump beam 1020 is split off the output of the pump laser 1010. Similar to the design in FIG. 4, a variable or tunable delay path is provided to guide the bypass pump beam 1020 and control the amount of the optical delay so that the pulses in the bypass pump beam 1020 is synchronized in time with optical pulses in the FWM signal 1043. This delay can be controlled by, e.g., using the output for a CARS measurement and maximizing the CARS signal.

The output module in FIG. 10 includes a dichroic mirror 1060 that reflects the signal 1041 into the fiber 1090 while transmitting both the blue-shifted FWM signal 1043 and light at the pump wavelength. A second dichroic mirror 1070 is provided to receive the transmitted light from the dichroic mirror 1060 by transmitting only the blue-shifted FWM signal 1043 while reflecting light at the pump wavelength. The bypass pump beam 1020 is directed to the second dichroic mirror 1070 in the way shown so that the bypass pump beam 1020 and the FWM signal 1043 are combined as the output of the device in FIG. 10.

Notably, different from the devices in FIGS. 4 and 9, the idler signal 1041 output by the PCF 840 is fed into a feedback optical path 1090, which can be a passive fiber, and is then coupled back as an optical input into the PCF 1040. Therefore, the PCF 1040 receives two input beams at two different wavelengths: the pump beam 1012 of pump optical pulses at the pump wavelength and the idler signal 1041 with idler optical pulses at the idler wavelength. An optical combiner 1030, e.g., a fiber coupler, can be used to combine the pump beam 1012 and the idler signal 1041 into the PCF 1040. This feedback optical path 890 turns the device in FIG. 10 into an optical parametric amplifier (OPA) or oscillator (OPO). The length of the passive fiber 1090 is chosen so the repetition rate of the OPA/OPO matches that of the pump laser 1010.

In some implementations of FIG. 10, it is maybe necessary to include a spectral bandpass filter 1080 in the optical path of the idler signal 1041 to control the spectral property of the feedback idler 1041. The filter 1080 can have a center wavelength that matches the center idler wavelength of the generated idler and has a desired spectral bandwidth to prevent excessive spectral broadening occurring over many roundtrips in the feedback loop formed by the fiber 1090. The spectral broadening in the idler signal 1041 can degrade the pulse quality and prevent self-consistent parametric oscillations, and therefore, is undesirable. The filter 1080 is used to reduce or eliminate such spectral broadening and can be located at a suitable location in the optical path of the idler signal 1041. The example in FIG. 10 shows that the filter 1080 is at an exemplary location between an optical collimator at the input port of the fiber 1090 and the dichroic mirror 1060 that reflects the signal 1041 into the fiber 1090. Another optical collimator may be used at the output of the PCF 1040 to collimate the output of the PCF 1040.

Figure 11A:
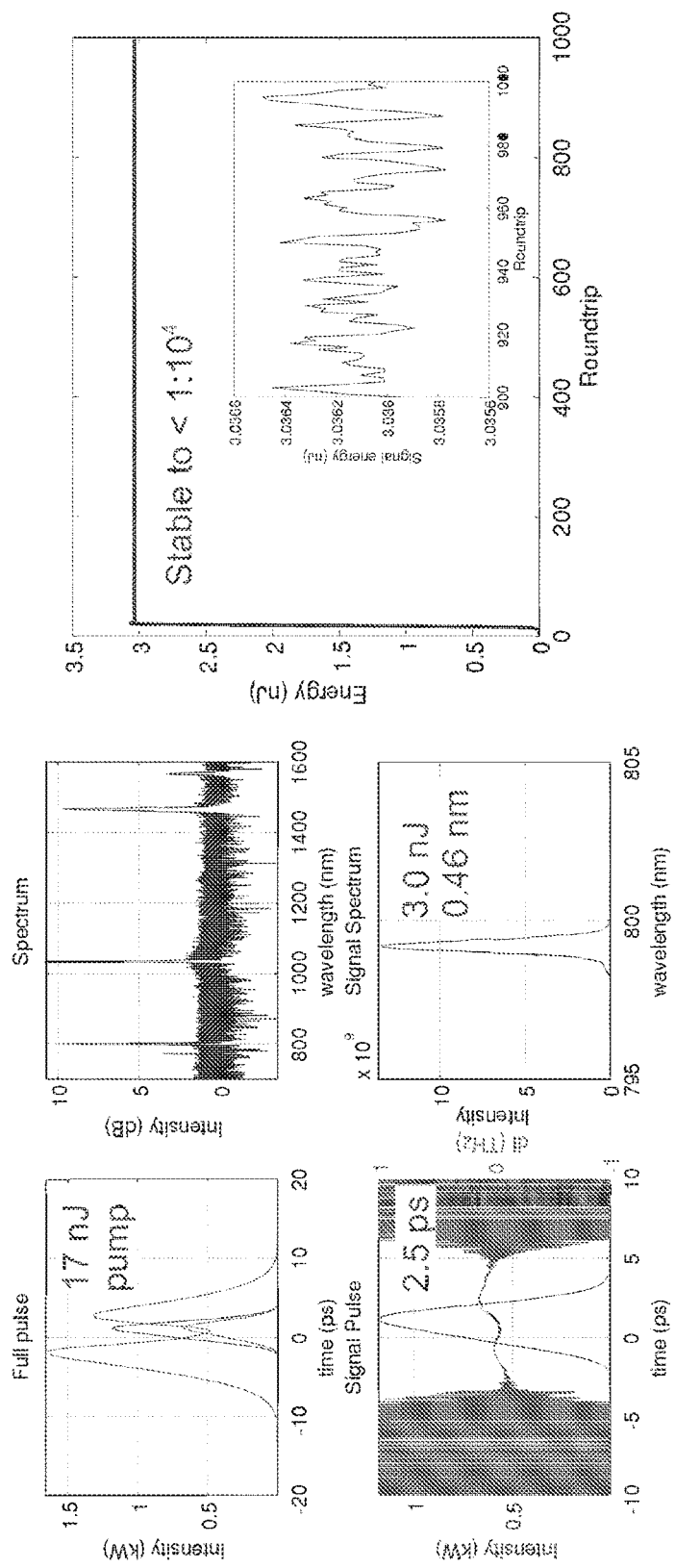
FIG. 11A shows measurements of the device in FIG. 10.
Figure 11B:
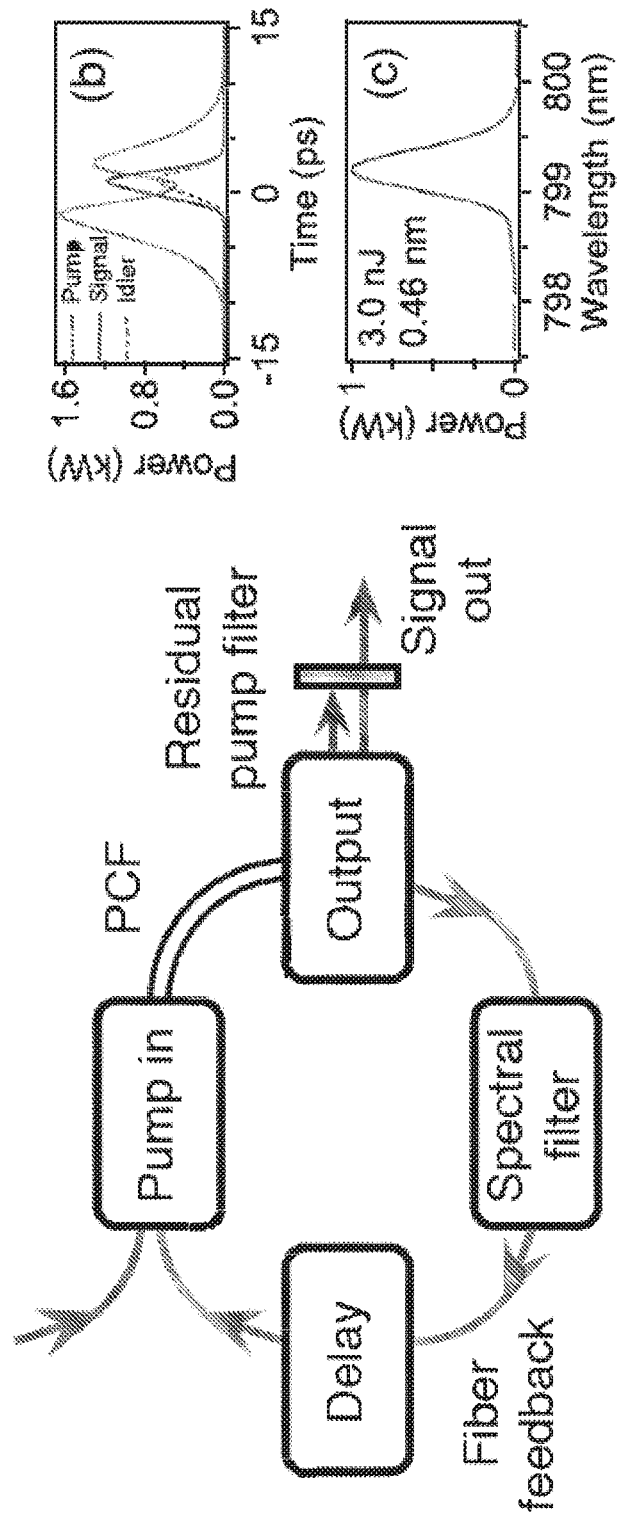
FIG. 11B shows a simulation model for a FWM fiber-OPO design where, in order to synchronize to the 54 MHz repetition rate of the pump fiber laser, 3.5 m of fiber with 8.2 µm core diameter and 0.14 NA is provided; the spectral filter has 2 nm bandwidth around 1468 nm, and the feedback delay is 10.2 ps; The output signal pulses have 3.0 nJ of pulse energy corresponding to 18% conversion, 0.46 nm bandwidth and 2.5 ps duration; The pulse energy is stable within 1:104 over more than 1000 roundtrips; The idler pulses are practically unaffected in the fiber feedback segment given the dispersion and non-linear lengths $L_D \approx 150$ m and $L_{NL} \approx 21$ m. The top insert shows the converged output pulses and the bottom insert shows the signal spectrum.

FIG. 11A shows the results of numerical simulations for a converged cavity solution based on a self-consistent OPO cavity model in FIG. 11B. The delay module in FIG. 11B corresponds to the optical delay by the feedback path 1090 in FIG. 10. Simulation results are for self-consistent OPO cavity with 21 cm of PCF and 3.5 m of feedback fiber. Input pump has 2.2 kW peak power and 7.5 ps duration. The spectral filter for filtering the feedback idler light has a 2-nm bandwidth around 1468 nm. The amount of the idler feedback can be set by the transmission of the filter which is set to be 5% for the simulations and the synchronization delay in the idler feedback loop is set to 10.2 ps for the simulations. The complex evolution of the free-running OPO leads to energy owing between the phase-matched central spectral peak and secondary peaks. The narrow spectral filter for filtering the idler can be used to stabilize the OPO by suppressing the growth of the secondary peaks. The signal pulses generated from the OPO can be combined with a portion of the pump pulses picked-off before the OPO. The combined beams can then be sent to a laser-scanning microscope to drive coherent Raman scattering imaging of biological and molecular samples.

Figure 12:
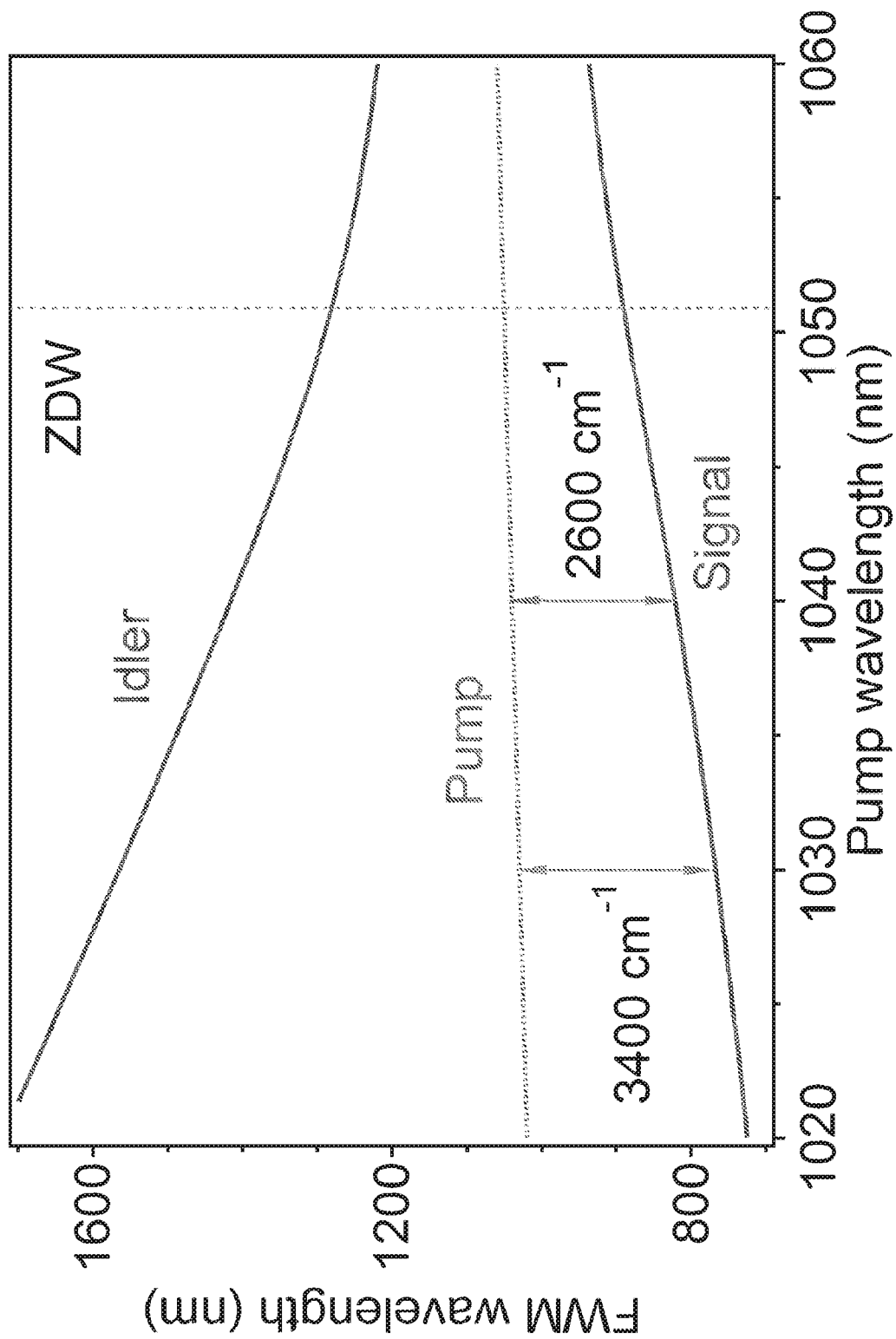
FIG. 12 shows an exemplary calculated tuning curve for a PCF.

Tuning of the OPO device in FIG. 10 can be accomplished by changing the pump fiber laser wavelength and tuning the spectral filter to the corresponding idler bandwidth. The calculated tuning curve for a typical PCF is shown in FIG. 12 where tuning curve is calculated from FWM phase-matching in a PCF with a zero-dispersion wavelength (ZDW) of 1051 nm.

The OPO device in FIG. 10 can be implemented by using various components. Here are some examples of various components. For example, a laser source based on Yb-doped optical fibers can be used by delivering pulses of duration ~7 ps with wavelength tunable from 1030-1040 nm. The PicoFYb product from TOptica Photonics AG, Germany can be used as a picosecond fiber oscillator. Amplification to powers ~1-5 W can be achieved using large core (20-30 um diameter) step-index optical fiber amplifiers, or divided pulse amplification in single-mode optical fiber.

In some implementations, the pump beam can be coupled into a normal-dispersion single mode PCF with a zero-dispersion wavelength around 1050-1060 nm Coupling can be done through a dichroic mirror or a fiber-fused wavelength division multiplexer (WDM). The generated signal is coupled out using a dichroic mirror or fiber WDM, and the idler is fed back through a passive fiber including a fiber optical delay line. The feedback beam is then combined with the incoming pump with either a dichroic or a WDM.

Frequency conversion may be accomplished using a dispersion engineered optical fiber. The fiber should have normal chromatic dispersion at the pump wavelength to provide narrowband, widely spaced frequency conversion. One of ways to engineer the dispersion curve around an optical wavelength of 1 um is using the photonic crystal fiber technology. The wavelength of the signal can be tuned either by changing the wavelength of the pulsed source, or by choosing a fiber with a different dispersion curve. An example of a suitable fiber product is the large mode area (LMA) fiber series from NKT Photonics A/S, Denmark.

In other implementations, the fiber frequency conversion can also be seeded by a diode pumped solid-state ps pulsed laser, such as the High Q picoTRAIN. Also, the dispersion engineered optical fiber could be replaced by a non-linear crystal such as periodically-poled lithium niobate, where the frequency conversion can be tuned by the poling period and the crystal temperature. In some applications, the residual pump pulses out of the PCF could be coupled out along with the signal and be used together for CRS. This would eliminate the need for separate beam combining with a picked-off beam. Since the pump pulses will have undergone distortion and spectral broadening during the FWM process, the distortion and the broadening should be controlled by mitigating related detrimental effects.

Figure 13:
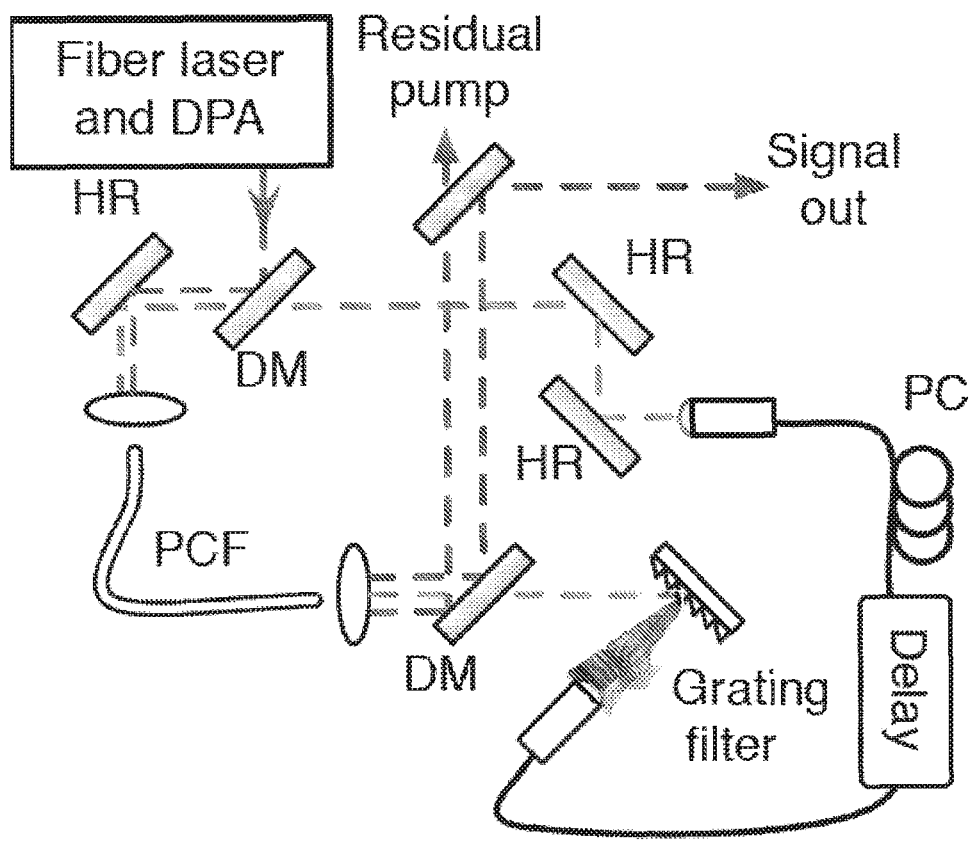
FIG. 13 shows another example of an OPO device based on the nonlinear FWM as modeled in FIG. 11A.

FIG. 13 shows another example of an OPO device based on the nonlinear FWM as modeled in FIG. 11A. The pump pulses are provided by a pump laser module that includes a fiber laser and a divided pulse amplifier. The pump is coupled in and the signal is extracted using dichroic mirrors. A filter with about 2 nm bandwidth is created by placing a 600 ln/mm grating 10 cm before the idler feedback collimator. A fiber delay line with up to 80 ps delay ensures synchronization. A fiber polarization controller matches the idler polarization to the pump. The PCF length is 30 cm, the feedback fiber is about 330 cm long and the free-space sections comprise about 36 cm of total length. Using a CW laser, the idler feedback is estimated to be 2-4%.

Figure 14:
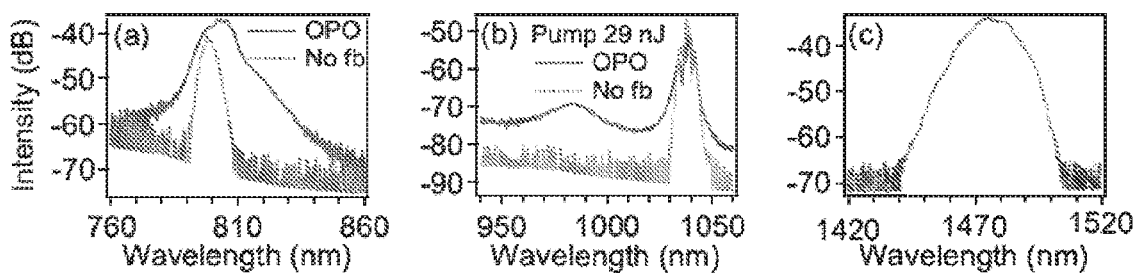
FIG. 14 shows experimental results for FWM fibber-OPO without spectral filtering, where the output spectra for OPO (solid) and single-pass (dotted) configurations are shown for (a) signal, (b) residual pump and (c) spontaneous idler

Preliminary experiments using the device in FIG. 13 were performed with the grating replaced by a mirror. This helps align the cavity and synchronize the delay without having to simultaneously tune the filter to the still uncertain idler wavelength. FIG. 14 shows the unfiltered OPO output after delay synchronization. With 29 nJ of pump pulse energy in the PCF, more than 5 nJ of signal can be generated. The signal bandwidth is about 13 nm, consistent with the typical bandwidth from the oscillating output. If the feedback is blocked, spontaneous FWM produces a signal with about 1 nJ pulse energy and bandwidth of about 4 nm. The corresponding spontaneous idler also exhibits a broad spectrum and is centered around 1470-1480 nm, in good agreement with simulations. Preliminary noise measurements of the filter-less OPO indicate a signal RIN of about −90 dBm/Hz, 20 dBm higher than the FWM OPA. This is expected given the oscillatory behavior seen in simulations. Using a spectral filter inside the cavity can obtain the stable narrow-band operation predicted in simulations.

The OPO devices in FIGS. 10 and 13 and other related device designs can be used to perform direct frequency conversion of ps pulses in optical fiber, allowing for greater mechanical integration as compared to solid-state sources. Such direct conversion of ps pulses can be obtained without having the undesired spectral broadening, and can be achieved using four-wave mixing in glass without frequency doubling before frequency conversion. The four-wave mixing at normal dispersion produces narrow bandwidth signal and idler fields with widely spaced frequencies, as compared to broadband and closely spaced fields at anomalous or zero dispersion. The FWM process can be scalable to high powers comparable to existing CARS solid-state sources. In some designs, the OPO can be designed to start oscillation from noise, thus eliminating the need for an extra seed. This design simplifies the frequency tuning.

An OPO based on the design in FIG. 10 or 13 can offer better noise performance than an optical parametric amplifier due to the stabilizing effect of cavity feedback. This should be advantageous for sensitive applications like SRS microscopy. Such an OPO is more efficient than various corresponding parametric amplifiers due to cavity feedback. The inclusion of a spectral filter is to prevent unwanted spectral broadening and to allow for stable self-consistent operation. The use of picosecond pulses simplifies fiber feedback and the low power idler pulse feedback can be essentially unaffected by dispersion and non-linearity over a few meters of fiber.

The above two-color ps pulse sources can be used in CRS imaging and spectroscopy for biological and medical sciences. The pulses can be coupled into a microscope system to be focused onto a biological sample. This can be done in a laboratory or clinical setting. The fiber-based nature of the proposed system is also optimal for coupling into a CRS imaging endoscope for in-vivo clinical medical imaging. We expect that the feedback in the OPO will reduce noise in the generated signal pulses, making the system well-suited to sensitive excitation schemes such as SRS microscopy.

While this patent document contains many specifics, these should not be construed as limitations on the scope of an invention or of what may be claimed, but rather as descriptions of features specific to particular embodiments of the invention. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Only a few implementations are disclosed. However, variations and enhancements of the described implementations and other implementations can be made based on what is described and illustrated in this patent document.

What is claimed is what is described and illustrated, including:

1. An optical device for producing optical pulses based on four wave mixing (FWM) to produce two input light beams at two different optical wavelengths for performing coherent anti-Stokes Raman scattering (CARS) microscopy, comprising:

a pump laser module to produce a FWM pump laser beam having FWM pump laser pulses at a FWM pump laser wavelength;

a segment of fiber having an input port and an output port, the input port coupled to receive the FWM pump laser beam and configured to exhibit normal optical dispersion at the FWM pump laser wavelength in FWM as a nonlinear optical four wave mixing medium to convert energy at the FWM pump laser wavelength into a four wave mixing signal as a first input light beam for CARS microscopy by performing the four wave mixing based on the FWM pump laser at the FWM pump laser wavelength and an idler signal at an idler wavelength longer than the laser pump wavelength, wherein a signal wavelength of the four wave mixing signal is shorter than the FWM pump laser wavelength and the idler wavelength, wherein the segment of fiber with normal optical dispersion at the FWM pump laser wavelength is configured to produce the four wave mixing signal having spectrally narrow FWM sidebands with large frequency shifts;

a seed laser configured to produce low-power continuous wave light at a power level lower than the FWM pump laser beam and coupled to the input port of the segment of fiber to inject continuous wave seed laser light at the idler wavelength with a narrow spectral width into the segment of fiber to coexist with the FWM pump laser pulses inside the segment of fiber as a continuous wave seed for initiating the idler signal for the four wave mixing in the segment of fiber to, in combination with the normal optical dispersion of the segment of fiber at the FWM pump laser wavelength, avoid generation of broad spectra in producing the four wave mixing signal in order to produce the spectrally narrow FWM sidebands with large frequency shifts;

a pump delay path coupled to receive a portion of the FWM pump laser beam as a bypass pump laser beam that does not enter the segment of fiber exhibiting normal optical dispersion at the FWM pump laser wavelength and is bypassed to be used as a second input light beam for CARS microscopy; and an output port coupled to the output port of the segment of fiber to select the four wave mixing signal at the signal wavelength from light output by the segment of fiber as a signal output without including light at a wavelength different from the signal wavelength, and coupled to the pump delay path to receive the bypass pump laser beam for CARS microscopy, the output port configured to combine the bypass pump laser beam and the four wave mixing signal as two input light beams at two different optical wavelengths for CARS microscopy.

2. The device as in claim 1, wherein:
the pump laser module includes a pump laser to produce pulsed pump laser light and an optical amplifier placed downstream from the pump laser to amplify the pulsed pump laser light as the FWM pump laser beam.

3. The device as in claim 2, wherein the optical amplifier includes a fiber amplifier.

4. The device as in claim 2, wherein the optical amplifier includes a divided pulse amplifier.

5. The device as in claim 1, wherein the segment of fiber includes a photonic crystal fiber.

6. The device as in claim 1, wherein the pump delay path has a length to cause a delay that synchronizes pulses in the bypass pump laser beam with pulses in the four wave mixing signal at the output port.

7. The device as in claim 1, wherein the output port includes a dichroic optical element that separates the four wave mixing signal at the signal wavelength from light at the idler wavelength and light at the laser pump wavelength.

8. The device as in claim 1, wherein the pump laser module produces the FWM pump laser pulses with a pulse duration in the picosecond range.

9. The device as in claim 1, wherein the pump laser module produces the FWM pump laser pulses with a pulse duration from 1 picosecond to 10 picoseconds.

10. The device as in claim 1, comprising:
a laser tuning controller coupled to the pump laser module or the seed laser and configured to tune a wavelength of the pump laser module or the seed laser to achieve tuning of the signal wavelength of the four wave mixing signal.

11. The device as in claim 1, comprising:
a laser tuning controller coupled to the pump laser module and the seed laser and configured to tune a wavelength of the pump laser module to provide a wide tuning of the signal wavelength of the four wave mixing signal, and to control a wavelength of the seed laser to achieve a fine tuning of the signal wavelength of the four wave mixing signal.

12. The device as in claim 1, comprising:
a feedback optical loop having an input terminal coupled to receive at least a portion of the idler signal at the idler wavelength exported by the output port of the segment of fiber and an output terminal coupled to the input port of the segment of fiber to feed the received portion of the idler signal into the segment of fiber to form an optical parametric amplification loop.

13. The device as in claim 12, comprising:
a spectral passband filter that transmits light at the idler wavelength and is coupled an optical path of the idler signal between the output port of the segment of fiber and the input port of the segment of fiber to filter light to have a narrow spectral width.

14. The device as in claim 1, wherein the FWM pump laser wavelength and the shorter signal wavelength of the four wave mixing signal have a difference that is tunable between 140 nm and 300 nm.

15. The device as in claim 1, wherein the pump laser module is tunable to tune the FWM pump laser wavelength from 1020 nm to 1060 nm to generate the signal wavelength of the four wave mixing signal that is blue-shifted at a wavelength between 720 nm and 920 nm.

16. The device as in claim 1, wherein the pump laser module is tunable to tune the FWM pump laser wavelength from 1030 nm to 1040 nm to generate the signal wavelength of the four wave mixing signal that is blue-shifted at a wavelength between 770 nm and 820 nm.

17. The device as in claim 1, wherein the device is structured to produce a narrow gain bandwidth compared to a broad gain bandwidth when the segment of fiber exhibits anomalous or zero optical dispersion at the FWM pump laser wavelength.

18. An optical device for producing optical pulses, comprising:
a fiber source laser to produce laser pulses at a first laser wavelength as pump light;
a segment of fiber coupled to receive the laser pulses from the fiber source laser and configured to exhibit normal optical dispersion to the pump light at the first laser wavelength as a nonlinear optical four-wave mixing medium, where seed laser light at a second laser wavelength longer than the first laser wavelength in the segment of fiber coexists with the laser pulses inside the segment of fiber to cause generation of light at a third laser wavelength shorter than the first laser wavelength and the second laser wavelength via nonlinear four-wave mixing inside the segment of fiber;
an optical fiber feedback path that is coupled to the segment of fiber and feeds a portion of generated light at the third laser wavelength back to the segment of fiber to mix with the light at the first wavelength, and the seed light at the second wavelength, wherein the optical feedback is configured to sustain an optical parametric oscillation;
a tunable optical delay path coupled to the fiber source laser to receive a portion of the light of the laser pulses at the first laser wavelength to cause a delay in the received portion of the light at the first laser wavelength as a pump beam at the first laser wavelength; and
an output device coupled to receive the pump beam at the first laser wavelength from the tunable optical delay path and the light at the third laser wavelength from the segment of fiber while blocking residual light at the first and second laser wavelengths from the segment of fiber to produce a combined optical output in which the pump beam at the first laser wavelength from the tunable optical delay path and the light at the third laser wavelength are synchronized.

19. The device as in claim 18, comprising:
a fiber coupler coupled to the optical fiber feedback path and the segment of fiber to direct the laser pulses at the first laser wavelength from the fiber source laser and the portion of the generated light at the third laser wavelength from the optical fiber feedback path into the segment of fiber.

20. The device as in claim 18, comprising:
an optical bandpass filter placed in an optical path of the optical fiber feedback path to remove light at wavelengths other than the third wavelength from the optical fiber feedback path.

21. A method for generating optical pulses, comprising:
operating a fiber source laser to produce laser pulses at a first laser frequency as pump light;
coupling a segment of fiber which exhibits normal optical dispersion to the pump light at the first laser wavelength and is a nonlinear optical four-wave mixing medium to receive the laser pulses from the fiber source laser to mix with seed laser light at a second laser frequency different from the first laser frequency inside the segment of fiber to cause generation of light at a third laser frequency different from the first laser frequency and the second laser frequency via nonlinear four-wave mixing inside the segment of fiber;
feeding a portion of generated light at the third laser wavelength via a fiber feedback loop back to the segment of fiber to mix with the light at the first wavelength, and the seed light at the second wavelength to sustain an optical parametric oscillation;

operating a tunable optical delay path coupled to the fiber source laser to receive a portion of the light of the laser pulses at the first laser wavelength to cause a delay in the received portion of the light at the first laser wavelength as a pump beam at the first laser wavelength; and operating an output device, that is coupled to receive the pump beam at the first laser wavelength from the tunable optical delay path and the light at the third laser wavelength from the segment of fiber, to block residual light at the first and second laser wavelengths from the segment of fiber and to produce a combined optical output in which the pump beam at the first laser wavelength from the tunable optical delay path and the light at the third laser wavelength are synchronized.

22. The method as in claim 21, comprising:
tuning the optical parametric oscillation in frequency by adjusting the first wavelength of the source laser.

23. The method as in claim 22, comprising:
tuning the optical parametric oscillation in frequency by adjusting a frequency of light that is fed back to the segment of fiber.

* * * * *